US010350432B2

(12) United States Patent
John et al.

(10) Patent No.: US 10,350,432 B2
(45) Date of Patent: *Jul. 16, 2019

(54) METHOD AND APPARATUS FOR PREVENTING NEURODEGENERATION

(71) Applicant: The Jackson Laboratory, Bar Harbor, ME (US)

(72) Inventors: Simon W. M. John, Bar Harbor, ME (US); Michael Anderson, Bar Harbor, ME (US); Richard Libby, Bar Harbor, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/668,764

(22) Filed: Aug. 4, 2017

(65) Prior Publication Data

US 2017/0333732 A1 Nov. 23, 2017

Related U.S. Application Data

(63) Continuation of application No. 12/563,483, filed on Sep. 21, 2009, now Pat. No. 9,789,336, which is a continuation-in-part of application No. 11/409,067, filed on Apr. 24, 2006, now abandoned.

(60) Provisional application No. 60/674,311, filed on Apr. 25, 2005.

(51) Int. Cl.
*A61N 5/10* (2006.01)
*A61N 5/00* (2006.01)
*A61N 5/067* (2006.01)
*A61N 5/06* (2006.01)
*A61F 9/009* (2006.01)
*A61B 6/00* (2006.01)
*A61F 9/007* (2006.01)
*A61F 9/008* (2006.01)

(52) U.S. Cl.
CPC ............ *A61N 5/1017* (2013.01); *A61B 6/506* (2013.01); *A61F 9/009* (2013.01); *A61F 9/00781* (2013.01); *A61F 2009/00863* (2013.01); *A61N 5/103* (2013.01); *A61N 5/1049* (2013.01); *A61N 5/1077* (2013.01); *A61N 5/1084* (2013.01)

(58) Field of Classification Search
CPC .......... A61N 5/1017; A61N 2005/1091; A61N 5/1049; A61N 2005/105; A61N 5/1064; A61N 2005/1019; A61N 5/10; A61N 5/1001; A61N 5/1045; A61N 5/1077; A61N 5/1084; A61B 6/506; A61B 6/508; A61F 2009/00863

See application file for complete search history.

(56) References Cited

U.S. PATENT DOCUMENTS

| 7,496,174 B2 | 2/2009 | Gertner et al. |
| 7,535,991 B2 | 5/2009 | Gertner |
| 7,620,147 B2 | 11/2009 | Gertner et al. |
| 7,680,244 B2 | 3/2010 | Gertner et al. |
| 7,693,260 B2 | 4/2010 | Gertner et al. |
| 7,953,203 B2 | 5/2011 | Gertner et al. |
| 2008/0181362 A1 | 7/2008 | Gertner |
| 2008/0187098 A1 | 8/2008 | Gertner et al. |
| 2008/0187099 A1 | 8/2008 | Gertner |
| 2008/0187100 A1 | 8/2008 | Gertner |
| 2008/0187101 A1 | 8/2008 | Gertner |
| 2008/0187102 A1 | 8/2008 | Gertner |
| 2008/0192893 A1 | 8/2008 | Gertner |
| 2008/0212738 A1 | 9/2008 | Gertner et al. |
| 2008/0247510 A1 | 10/2008 | Gertner et al. |
| 2009/0003525 A1 | 1/2009 | Gertner et al. |
| 2009/0022274 A1 | 1/2009 | Gertner et al. |

OTHER PUBLICATIONS

The fact sheet of gamma vs x-ray comparison (retrieved the article from the website http://www.radsource.com/literature/PDFs/Gamma%20vs%20X-ray%20Comparison%20062509.pdf, on Aug. 15, 2011.*
'T Hart et al. Curr. Opin. Neurol. 2003. 16: 375-383.*
Anger. Neurotoxicology 1991. 12: 403-13.*
Tayebati. Mech. Ageing Dev. 2006. 127: 100-8.*
Wiggs, "Genetic Etiologies of Glaucoma", Arch Ophthalmol., vol. 125, p. 30 (Jan. 2007).
Antin, J.H., et al. "Selective Depletion of Bone Marrow T-Lymphocyte with Anti-CD5 Monoclonal Antibodies: Effective Prophylaxis for Graft-Versus-Host Disease in Patients with Hematologic Malignancies," Blood, (1991), 67, pp. 2139-2149.
DeWitte, T., et al. "Depletion of Donor Lymphocytes by Counterflow Centrifugation Successfully Prevents Acute Graft-Versus-Host Disease in Matched Allogeneic Marrow Transplantation," Blood, (1986), 67, pp. 1302-1308.
Maraninchi, D., et al. "Selective Depletion of Marrow-T Cytotoxic Lymphocytes (CD8) in the Prevention of Graft-Versus-Host Disease After Allogeneic Bone Marrow Transplantation," Transplant Int., (1988), 1, pp. 91-94.
Soiffer, R.J., et al. "Prevention of Graft-Versus-Host Disease by Selective Depletion of CD6-Positive T Lymphocytes From Donor Bone Marrow," J. Clin. Oncol., (1992), 10, pp. 1191-1200.

(Continued)

*Primary Examiner* — Chang-Yu Wang
(74) *Attorney, Agent, or Firm* — Pierce Atwood LLP

(57) ABSTRACT

A method for treating, preventing and/or reducing neurodegeneration in subjects with neurodegenerative disease, such as those neurodegenerative diseases that affect the eye, including glaucoma, using radiation, such as gamma radiation or X-ray radiation, either alone or together with a bone marrow transfer treatment. The method includes irradiating a targeted area of an animal, such as the eye region, with radiation, either alone or followed by injection with T-cell depleted bone marrow cells. Also a method for screening and/or selecting agents and/or treatment methods for inhibiting, treating and/or reducing neurodegeneration, particularly the neurodegeneration of the eye that occurs as a consequence of glaucoma.

29 Claims, 8 Drawing Sheets

Specification includes a Sequence Listing.

(56) References Cited

OTHER PUBLICATIONS

Filipovich, A.H., et al. "T Cell Depletion with Anti-CD5 Immunotoxin in Histocompatible Bone Marrow Transplantation," Transplantation, (1990), 50, pp. 410-415.
Wagner, J.E., et al. "Bone Marrow Graft Engineering by Counterflow Centrifugal Elutriation: Results of a Phase I-II Clinical Trial," Blood, (1990), 75, pp. 1370-1377.
Herve, P., et al. "Removal of Marrow T Cells with OKT3-OKT11 Monoclonal Antibodies and Complement to Prevent Acute Graft-Versus-Host Disease," Transplantation, (1985), 39, pp. 138-143.
Belkacemi, Y., et al. "Total-Body Irradiation before Bone Marrow Transplantation for Acute Leukemia in First or Second Complete Remission," Strahlenther Onkol., (1998), 174, No. 2, pp. 92-104.
Burt, Richard K., et al. "Treatment of Autoimmune Disease by Intense Immunosuppressive Conditioning and Autologous Hematopoietic Stem Cell Transplantation," Blood, (1998), 92, No. 10, pp. 3505-3514.
Horning, S.J., et al. "Fractionated Total-Body Irradiation, Etoposide, and Cyclophosphamide Plus Autografting in Hodgkin's Disease and Non-Hodgkin's Lymphoma," J. Clin. Oncol., (1994), 12, pp. 2552-2558.
Thomas, E.D. and Storb, R. "Technique for Human Marrow Grafting," Blood, (1970), 36, No. 4, pp. 507-515.
Buckner, C.D. et al. "Marrow Harvesting from Normal Donors," Blood, (1984), 64, pp. 630-634.
Bortin, M.M. and Bucker, C.D. "Major Complications of Marrow Harvesting for Transplantation," Exp. Hematol., (1983), 11, pp. 916-921.
Kessinger, A., and Armitage, J.O. "Harvesting Marrow for Autologous Transplantation from Patients with Malignancies," Bone Marrow Transplant, (1987), 2, pp. 15-18.
Nutting, et al. "Intensity Modulated Radiation Therapy: A Clinical Review," The British Journal of Radiology, (2000), 73, pp. 459-469.
Sanderson, R.J. and Ironside, J.A.D. "Squamous Cell Carcinomas of the Head and Neck," BMJ, (2002) 325, No. 7368, pp. 822-827.
Lumbroso-Le Rouic, et al. "125I Plaque Brachytherapy for Anterior Uveal Melanomas," Eye, (2004), 18, pp. 911-916.
Kipnis, J., et al. "Low-dose Irradiation Promotes Survival of Injured Neurons in the Central Nervous System via Homeostatis-Driven Proliferation of T-Cells," European Journal of Neuroscience, (2004), 19, pp. 1191-1198.
Bakalash, S., et al. "T-Cell-Based Vaccination for Morphological and Functional Neuroprotection in a Rat Model of Chronically Elevated Intraocular Pressure," J. Mol. Med., (2005), 83, No. 11, pp. 904-916.
Takeda, A., et al. "Late Retinal Complications of Radiation Therapy for Nasal and Paranasal Malignancies: Relationship Between Irradiated-Dose Area and Severity," Int. J. Radiation Oncology Biol. Phys., (1999), 44, No. 3, pp. 599-605.
Phillips, C., et al. "Retinoblastoma: Review of 30 Years' Experience with External Beam Radiotherapy," Australasian Radiology, (2003), 47, pp. 226-230.
Ritch, R., et al. "The Glaucomas," (1996), pp. 717-725,1507-1531, Mosby, St. Louis.
Weinreb, R.N. & Khaw, P.T. "Primary Open-Angle Glaucoma," Lancet, (2004), 363, pp. 1711-1720.
Heijl, A., et al. "Reduction of Intraocular Pressure and Glaucoma Progression," Arch. Ophthalmol., (2002) 120, pp. 1268-1279.
"Comparison of Glaucomatous Progression Between Untreated Patients with Normal-Tension Glaucoma and Patients with Therapeutically Reduced Intraocular Pressures—Collaborative Normal-Tension Glaucoma Study Group," Am. J. Ophthalmol., (1998), 126, pp. 487-497.
John, S.W., et al. "Mouse Genetics: A Tool to Help Unlock the Mechanisms of Glaucoma," J. Glaucoma, (1999), 8, pp. 400-412.
John, S.W. et al "Essential Iris Atrophy, Pigment Dispersion, and Glaucoma in DBA/2J Mice," Invest. Ophthalmol. Visual Sci., (1998), 39, pp. 951-962.
Chang, B., et al. "Interacting Loci Cause Severe Iris Atrophy and Glaucoma in DBA/2J Mice," Nat. Genet., 21, pp. 405-409.
Anderson, M.G., et al. "Mutations in Genes Encoding Melanosomal Proteins Cause Pigmenting Glaucoma in DBA/2J Mice," Nat. Genet., (2002), 30, pp. 81-85.
Quigley, H.A. "Neuronal Death in Glaucoma," Prog. Retin. Eye Res., (1998), 18, pp. 39-57.
Nickells, R.W. "The Molecular Biology of Retinal Ganglion Cell Death: Caveats and Controversies," Brain Res. Bull., (2004), 62, pp. 439-446.
Raff, M.C., et al. "Axonal Self-Destruction and Neurodegeneration," Science, (2002), 296, pp. 868-871.
Good, Robert A. "Progress Towards Production of Immunologic Tolerance with No or Minimal Toxic Immunosuppression for Prevention of Immunodeficiency and Autoimmune Diseases," World Journal of Surgery, (Jul. 2000), 24, No. 7, pp. 797-810.
Clift, R.A., et al. "Allogeneic Marrow Transplantation in Patients with Chronic Myeloid Leukemia in the Chronic Phase: A Randomized Trial of Two Irradiation Regimens," Blood, (1991) 77, No. 8, pp. 1660-1665.
Matthews, D.C., et al. "Development of a Marrow Transplant Regimen for Acute Leukemia Using Targeted Hematopoietic Irradiation Delivered by 131I-Labeled Anti-CD45 Antibody, Combined With Cyclophosphamide and Total Body Irradiation," Blood, (1995), 85, No. 4, pp. 1122-1131.
Mackall, C.L., et al. "Distinctions Between CD8+ and CD4+ T-Cell Regenerative Pathways Result in Prolonged T-Cell Subset Imbalance After Intensive Chemotherapy," Blood, (1997), 89, No. 10, pp. 3700-3707.
Roux, E., et al. "Analysis of T-Cell Repopulation After Allogeneic Bone Marrow Transplantation: Significant Differences Between Recipients of T-Cell Depleted and Unmanipulated Grafts," Blood, (1996), 87, No. 9, pp. 3984-3992.
Champlin, R., et al. "T-Cell Depletion to Prevent Graft-Versus-Host Disease After Bone Marrow Transplantation," Hematol. Oncol. Clin. North Am., (1990), 4, pp. 687-698.
O'Reilly, R.J., et al. "T-Cell Depletion and Allogeneic Bone Marrow Transplantation," Semin. Hematol., (1992), 29, No. 1, pp. 20-26.
Martin, P.J., et al. "Effects of In Vitro Depletion of T Cells in HLA-Identical Allogeneic Marrow Grafts," Blood, (1985), 36, pp. 664-672.
Prentice, H.G., et al. "Use of Anti-T-Cell Monoclonal Antibody OKT3 to Prevent Acute Graft-Versus-Host Disease in Allogeneic Bone Marrow Transplantation for Acute Leukemia," Lancet, (1982), 1, pp. 700-703.
Waldmann, H., et al. "Elimination of Graft-Versus-Host Disease by In-Vitro Depletion of Alloreactive Lymphocytes with a Monoclonal Rat Anti-Human Lymphocyte Antibody (CAMPATH-1)," Lancet, (1984), 2, 483-486.
The fact sheet of radiation to the eye retrieved from the website: www.aboutcancer.com/radiation_to_the_eye.htm on Nov. 5, 2015.
Johnson et al. Invest. Ophthalmol. Vis. Sci. 2015; 56:412-419.
Chang, Korean J. Ophthalmol. 201 O: 24:384-385.
Janssen et al. Prog. in Retinal and Eye Res. 2013; 37:31-67.
Borges et al. J. Cell Science. 1999; 112:4315-4324.
Wilner et al. Strahlenther Onkol, 2001. Aug.; 177: 404-9, abstract. http://www.radsource.com/literature/PDFs/Gamma%20vs%20X-ray%20Comparison%20062509.pdf, on Aug. 15, 2011.
John SWM, Smith RS, Hawes NL, Savinova OV, Chang B, Turnbull D, Davisson MT, Roderick TH, Heckenlively JR. Essential iris atrophy, pigment dispersion and glaucoma in DBA2/J mice. Invest. Ophthalmol. Vis. Sci. 39:951-962 (1998).
Howell GR, Libby RT, Marchant JK, Wilson LA, Cosmal M, Smith RS, Anderson MG, John SWM. Absence of glaucoma in DBA/2J mice homozygous for wild-type version of Gpnmb and Tyrp1. BMC Genet 8:45 (2007).
Vasanth Rao, Robert Lalane, III, Corey Morris, Padma Iyer. Ophthal & Pharmacology, Ophthalmology, Duke University, Durham, NC. Topical Application of Rho Kinase Inhibitor Decreases Intraocular Pressure and Prevents the Loss of Retinal Ganglion Cells in the Aging DBA/2J Mice, Association for Research in Vision and Ophthalmology, Inc. (May 3, 2011).

(56) References Cited

OTHER PUBLICATIONS

Timothy A. Sullivan, Eldon E. Geisert, Jessica Hines-Beard, and Tonia S. Rex. Systemic Adeno-Associated Virus-Mediated Gene Therapy Preserves Retinal Ganglion Cells and Visual Function in DBA/2J Glaucomatous Mice Hum. Gen. Ther. 22(1):1191-1200 (Oct. 2011).
Manik Goel, Adam E Sienkiewicz, Renata Picciani, Jianhua Wang, Richard K. Lee, Sanjoy K. Bhattacharya, Cochlin, Intraocular Pressure Regulation and Mechanosensing, PLOS One (Apr. 4, 2012).
Nagaraju M, Saleh M, Porciatti V. IOP-dependent retinal ganglion cell dysfunction in glaucomatous DBA/2J mice. Invest Ophthalmol. Vis. Sci.48(10):4573-9 (Oct. 2007).
Zhong L, Bradley J, Schubert W, et al. Erythropoietin promotes survival of retinal ganglion cells in DBA/2J glaucoma mice. Invest. Ophthalmol .Vis. Sci. 48:1212-1218 (2007).
Ju W, Kim K, Angert M, et al. Memantine blocks mitochondrial OPA1 and cytochrome c release and subsequent apoptotic cell death in glaucomatous retina. Invest Ophthalmol Vis Sci. 50:707-716 (2009).
Matsubara A, Nakazawa T, Husain D, Iliaki E, Connolly E, Michaud NA, Gragoudas ES, Miller JW. Investigating the effect of ciliary body photodynamic therapy in a glaucoma mouse model. Invest. Ophthalmol. Vis. Sci. 47(6):2498-507 (Jun. 2006).
Wong AA, Brown RE. A neurobehavioral analysis of the prevention of visual impairment in the DBA/2J mouse model of glaucoma. Invest Ophthalmol Vis Sci. 53(9):5956-66 (Aug. 31, 2012).
Libby RT, Anderson MG, Pang I-H, Robinson Z, Savinova OV, Cosma 1M, Snow A, Wilson LA, Smith RS, Clark AF, John SWM. Inherited glaucoma in DBA/2J mice: pertinent disease features for studying the neurodegeneration. Vis. Neurosci. 22: 637-648 (2005).
Jakobs TC, Libby RT, Ben Y, John SWM, Masland RH. Retinal ganglion cell degeneration is topological but not cell type specific in DBA/2J mice. J. Cell. Biol. 171(2):313-325 (2005).
John SWM. Mechanistic insights to glaucoma provided by experimental genetics: The Cogan Lecture. Invest. Ophthalmol. Vis. Sci. 46:2650-2661 (2005).
Whitmore AV, Libby RT, John SWM. Glaucoma: thinking in new ways—a role for autonomous axonal self-destruction and other compartmentalized processes. Prog. Retin. Eye Res. 24:639-662 (2005).
Nickells RW, Howell GR, Soto I, John SWM. Under pressure: cellular and molecular responses in glaucoma. Annu Rev Neurosci 35: 153-179 (2012).
Cassandra L Schlamp, Yan Li, Joel A Dietz, Katherine T Janssen and Robert W Nickells, Progressive ganglion cell loss and optic nerve degeneration in DBA/2J mice is variable and asymmetric, BMC Neurosci. 7:66 (Oct. 3, 2006).
Howell GR, Macalinao D, Sousa G, Walden M, Soto I, Kneeland S, Barbay J, King B, Marchant J, Hibbs M, Stevens B, Barres B, Clark A, Libby R, John SWM. Molecular clustering identified complement and endothelin induction as early events in a mouse glaucoma. J. Clin. Invest. 121(4): 1429-1444 (2011).
Howell GR, Libby RT , Jakobs TC, Smith RS, Phalan FC, Barter JW, Barbay JM, Marchant JK, Mahesh N, Porciatti V, Whitmore A V, Masland RH, John SWM. Axons of retinal ganglion cells are insulted in the optic nerve early in DBA/2J glaucoma. J. Cell. Biol. 179: 1523-1537 (2007).
Anderson MG, Libby RT, Gould DB , Smith RS, John SWM. High-dose radiation with bone mar row transplant prevents neurodegeneration in an inherited glaucoma. Proc Natl Acad. Sci. USA 102:4566-4571 (2005).
Chang B, Smith RS , Hawes NL, Anderson MG, Zabaleta A, Savinova 0 , Roderick TH, Heckenlively JR Davisson MT, John SWM. Interacting loci cause severe iris atrophy and glaucoma in BA2/J mice. Nat. Genet 21 :405-409 (1999).
Anderson MG, Smith RS, Hawes NL, Zabaleta A, Chang B, Wiggs JL, John SWM. Mutations in genes encoding melanosomal proteins cause pigmentary glaucoma in DBA/2J mice. Nat. Genet 30:81-85 (2002).

Stevens B, Allen NJ, Vazquez LE, Howell GR, Christopherson KS , Nouri N, Micheva KD, Mehalow A, Huberman AD, Stafford B, Sher A, Litke AM, Lambris JD, Smith SJ, John SWM, Barres BA. The classical complement cascade mediates CNS synapse elimination. Cell 131:1164-1178 (2007).
Kalliopi Stasi , Dalia Nagel , Xiaoyan Yang , Rong-Fang Wang , Lizhen Ren , Steven M. Podos , Thom Mittag, John Danias. Complement Component 1Q (C1Q) Upregulation in Retina of Murine, Primate, and Human Glaucomatous Eyes Invest. Ophthalmol. Vis. Sci.. 47(3):1024-1029 (Mar. 2006).
John SW, Smith RS, Savinova OV, Hawes NL, Chang B, Turnbull D, Davisson M, Roderick TH, Heckenlively JR., "Essential Iris Atrophy, Pigment Dispersion, and Glaucoma in DBA/2J Mice," Invest. Ophthalmol. Vis. Sci. 39(6):951-62 (May 1998).
Burroughs SL, Kaja S, Koulen P. Quantification of deficits in spatial visual function of mouse models for glaucoma. Invest. Ophthalmol. Vis. Sci. 52(6):3654-9 (Jun. 1, 2011).
Inman DM, Lambert WS, Calkins DJ, Homer PJ. α-Lipoic Acid Antioxidant Treatment Limits Glaucoma-Related Retinal Ganglion Cell Death and Dysfunction. PLoS One. 8(6):e65389 (Jun. 5, 2013).
International Search Report and Written Opinion received in Appl. No: PCT/US2010/049449 dated Nov. 26, 2010.
Anderson et al.; "High-dose radiation with bone marrow transfer prevents neurodegeneration in an inherited glaucoma", PNAS, vol. 102, No. 12, pp. 4566-4571 (Mar. 2005).
Katz et al., "Automated suprathreshold screening for glaucoma: the Baltmore Eye Surgery", Investigative Ophthalmology & Visual Science, vol. 34, No. 12, pp. 3271-3277 (Nov. 1993).
Sarfarazi, "Recent advances in molecular genetics of glaucomas", Human Molecular Genetics, vol. 6, No. 10, pp. 1667-1677 (1997).
Valmaggia et al., "Low dose radiation for subfoveal choroidal neovascularization in age-related macular degeneration. A pilot study." Documenta Ophthalmologica, vol. 93, pp. 317-326 (1997).
Million, Rodney R. and Parsons, James T. "Radiation-Induced Eye Injury From Head and Neck Therapy," Front Radiat. Ther. Oncol., (1999), 32, pp. 21-33.
Anderson, M.G., et al. "High-Dose Radiation with Bone Marrow Transfer Prevents Neurodegeneration in an Inherited Glaucoma," PNAS, (2005), 102, No. 12, pp. 4566-4571.
Nag, Subir., et al. "The American Brachytherapy Society Recommendations for Brachytherapy of Uveal Melanomas," International Journal of Radiation Oncology, Biology, and Physics, (2003), 56, No. 2, pp. 544-555.
Devita, Vincent T., Hellman, Samuel, Rosenberg, Steven A. "Cancer, Principles, & Practice of Oncology," (1997), pp. 2109-2110, 2233-2238, Lippincott-Raven, Philadelphia.
Bechetoille, et al., "Glaucoma Surgery", Fundamentals of Clinical Opthalmology, Glaucoma, BMJ, 11, pp. 91-105 (2000).
Child, "Genetic Screening for glaucoma" Fundamentals of Clinical Opthalmology, Glaucoma, BMJ, 4, pp. 22-28 (2000).
Fraser, "Epidemiology of primary open angle glaucoma" Fundamentals of Clinical Opthalmology, Glaucoma, BMJ, 2, pp. 9-15 (2000).
Garway-Heath, et al. "Primary Glaucoma" Atlas of Clinical Ophthalmology Third Edition, 7, pp. 187-207 (2005).
Jonas, et al., "Primary glaucoma: optic disc features" Fundamentals of Clinical Opthalmology, Glaucoma, BMJ, 5, pp. 29-38 (2000).
Kirwan, et al. "Effect of B radiation on success of glaucoma drainage surgery in South Africa: randomized controlled trial" BMJ, pp. 1-6 (Oct. 5, 2006).
Miller, et al. "Trabeculectomy combined with B irradiation for congenital glaucoma" British Journal of Ophthalmology, 75, pp. 584-590 (1991).
Spaeth, "Principles of treatment of glaucoma" Fundamentals of Clinical Opthalmology, Glaucoma, BMJ, 8, pp. 62-76 (2000).
Khan, "The Physics of Radiation Therapy" Third Edition, 2003.
Anderson et al., "Mutations in genes encoding melanosomal proteins cause pigmentary glaucoma in DBA/2J mice", Nature Genetics, vol. 30, pp. 81-82 (Jan. 2002).
Kirwan, et al. "Beta irradiation: new uses for an old treatment: a review", Eye, vol. 17, pp. 207-215 (2003).
Osborne, et al., "Optic nerve and neuroprotection strategies", Eye, vol. 18, pp. 1075-1084 (2004).

(56) References Cited

OTHER PUBLICATIONS

Vladyka, et al. "Initial experience with gamma knife radiosurgery for advanced glaucoma", J. Neurosurg (Suppl. 3) vol. 93, pp. 180-183 (2000).
Vladyka, et al. "Glaucoma treated by gamma knife irradiation", J. Neurosurg., vol. 103, p. 192 (Jul. 2005).
Vladyka et al. "Progress in glaucoma treatment research: a nonrandomized prospective study of 102 patients with advanced refractory glaucoma treated by Leksell gamma knife irradiation" J. Neurosurg., vol. 102, pp. 214-219 (Jan. 2005).

\* cited by examiner

FIG. 1A
UNTREATED
FIG. 1B
TREATED
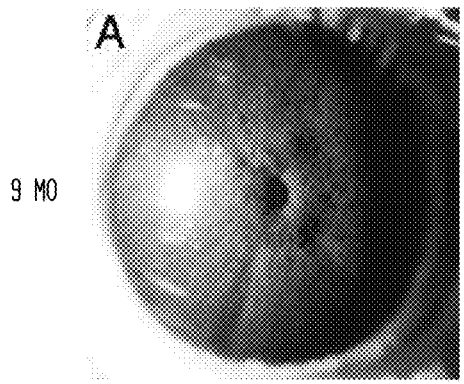
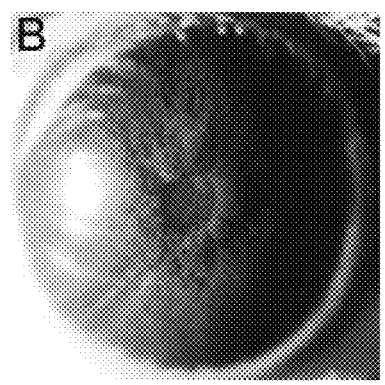
9 MO
FIG. 1C
UNTREATED
FIG. 1D
TREATED
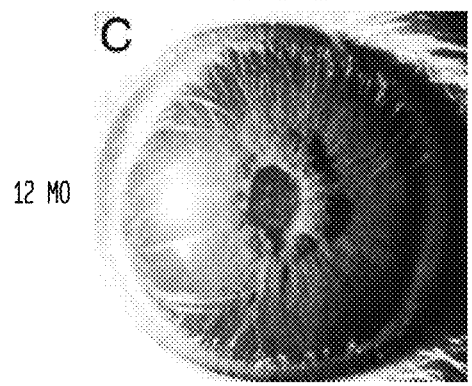
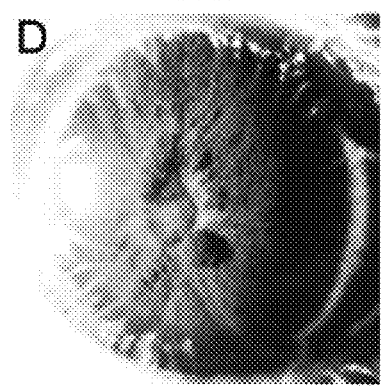
12 MO
FIG. 1E
UNTREATED
FIG. 1F
TREATED
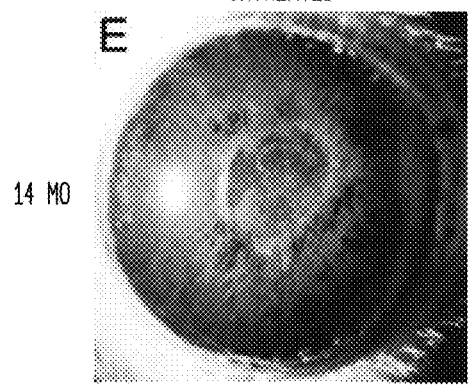
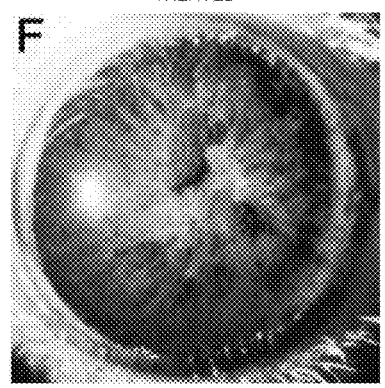
14 MO

EFFECT OF PART BODY IRRADIATION ON GLAUCOMATOUS OPTIC NERVE DAMAGE

SEQUENCE LISTING

```
<160> NUMBER OF SEQ ID NOS: 1

<210> SEQ ID NO 1
<211> LENGTH: 17217
<212> TYPE: DNA
<213> ORGANISM: Homo sapiens

<400> SEQUENCE: 1
gaagcctcac caagcctctg caatgaggtt cttctgtgca cgttgctgca gctttgggcc      60
tgagatgcca gctgtccagc tgctgcttct ggcctgcctg gtgtgggatg tgggggccag     120
gacagctcag ctcaggaagg ccaatgacca gagtggccga tgccagtata ccttcagtgt     180
ggccagtccc aatgaatcca gctgcccaga gcagagccag gccatgtcag tcatccataa     240
cttacagaga gacagcagca cccaacgctt agacctggag gccaccaaag ctcgactcag     300
ctccctggag agcctcctcc accaattgac cttggaccag gctgccaggc cccaggagac     360
ccaggagggg ctgcagaggg agctgggcac cctgaggcgg gagcgggacc agctggaaac     420
ccaaaccaga gagttggaga ctgcctacag caacctcctc cgagacaagt cagttctgga     480
ggaagagaag aagcgactaa ggcaagaaaa tgagaatctg gccaggaggt tggaaagcag     540
cagccaggag gtagcaaggc tgagaagggg ccagtgtccc cagacccgag acactgctcg     600
ggctgtgcca ccaggctcca gagaaggtaa gaatgcagag tggggggact ctgagttcag     660
caggtgatat ggctcgtagt gacctgctac aggcgctcca ggcctccctg cctgcccttt     720
```

-continued

```
ctcctagaga ctgcacagct agcacaagac agatgaatta aggaaagcac agcgatcacc    780
ttcaagtatt actagtaatt tagctcctga gagcttcatt tagattagtg gttcagagtt    840
cttgtgcccc tccatgtcag ttttcacagt ccatagcaaa aggagaaata aaaggaccgg    900
gtgagatgtg tctgcatatg agcagtagaa agttgtcaat tgtccctttt gaaaaactat    960
ccttttttga acctttgctc agattgttat ttgtacccttt tgatgttaaa atgacccttta   1020 tttatgaaat tacaatagat ttgggaaatg ataataagtg gtaagttttt gtttattttt   1080
aaatgttctt ccctggcaaa ataaagagat ggcacctctc tgtcagtttt cttaatatgt   1140
tgttctgaaa gttttcttac tcagtccaat ctgagaacct ctgcttttaa gtcatcagac   1200
aaattcttga gatggctttt tctgagaggc tcttctgttc atcctggtcc cttcttgcct   1260
aaaggtgagt ctgtgtgtgt gtgggggggg tgcggggtg aggtgttggg ggaggtcttc    1320
ttattagctg ggaagatggt atttgtgtca cttttgtga aagtgggctc ccaaatattc    1380
cctgttgagg aagtgttcta atcatgagga aataagcaag caaatccagt tgttggacaa   1440
ttagtttgga ctggtcaaag atgtcagtgc caaggaagaa agaaaaaagg ggtgggggaag   1500 ggcttgttct atattaaaga gactaaagaa atgtgttaac caaatgtagt gcatgagtct   1560
tgattggtgt cttcatccaa gggggaaaaa ggctatgagg aacaggtttg ggataactga   1620
ggcaatttga ctgctcatta ttatgttact gtattaatgt tcagtttctt ggtgagataa   1680
tgatactgtg gttgcgaagg ataaaatctt tgttctatgg agatacatgc ttaagtaccc   1740
agggtgaggc gtcaggatgt ctgcaatttg ctctcaaatg gttgaagaaa gactgcaaat   1800
atatagataa tgagagaaag aaaggtaaaa caactgtggc aaaatattaa taactggtga   1860
attacaaact ggtgaatcta agtatatggg gagcttattg tactattctt tcagttttc    1920 tataggcttg aaaagcttta aaattatgag aaaatatttc ctaaaaagag ccttctacgt   1980
gaaaggcaag ctcttcatag ctatggggtt agaaaaccta agagccagag cctggggatg   2040
accttgggca agttattgaa ccctctgcat cttcatttct tgtccataac ataacaaaga   2100
aaattcctgc tgtgaataat ttttgtgggg ttcacatgaa ataccctataa gatgtaaagg   2160 attttttaaaa aatgtttaga ttgttagaat tagaagagat ccaattctga attttacaac   2220
caaggaaagt gaagtcctaa gatgctaagg ggccaaggtt gcccagctgg tcagtggtag   2280
agcttgagac ttgaatctgt ggagacaatt gaaagaatca tcattaccag aagtgtgatg   2340
aggcattact tatttcagac tgttgaatga agttacattc tcaataaaaa ctcctgcatg   2400
tgtgtatgtg ggtgtgggtg gtgtgtgtgt gtgtgtacaa aaatagtggc aatgttttgc   2460 ctttttttttt cttttgtggt catttaacaa gtctttgggg atttattaga tgtgtttcct   2520
aattttatat tttttcttga tctttccagc tactccactt ttgaaataag gcaacatcc    2580 cattatattg aacaccaaac atggaagttc ttttctagta gtagatgttt ttcatgagca   2640
ggaaattaca ttagtacaag aatgtggaac tggaaaggga cctaatgagc atccggtacc   2700
gctggctgat ttttgcagat atggaaactg aggcccagag aggttattca gcttgtccat   2760
ggccatctac cagttagtgg caaagctcga attctggcct cttcctctga agttcagtga   2820 cttctttct ttttttttga gacagagttt cactcttgtt gcccaggcta gagtgtaatg    2880
gcacgatctt ggctcactga aacctctgcc tcccgggttc aagcaattct cctacctcag   2940
cctcctgagt agctgggatt ataggcatgt gccaccatgc ccggctaatt ttgtattttt   3000
agtagagaca gggtttcacc atgttggtca ggctagtctc gaactcctga cctcaggtga   3060
tctgccgacc tcggccttcc aaagcactgg gattacaggt gtgagccctc cctgtacatg   3120
```

```
gccatgaggt tcattgactt tcaagacctt cagctgacct ctggtttata gaccctaaag    3180
gtaaaagaca gaaaggtaca ggaatgcttg gaacaaaaga tctgtttcaa ggccagatct    3240
agggaaaagg gggcattctg gaggctggaa tataagtcta ggtatgcttt tttgcaggag    3300
tggcaagaac taggtgtgaa ggtttgggta gagaagctta gtgaggctga gtggacaaag    3360
gtaaggcctg agaaggcagc ctttctgtat tccacctgca actcaaattg ttaccaccac    3420
tttcttgatc atgtattaat agttgttatg tagaaaaaaa ttccttataa tcatagaaat    3480
cacttgttta tacatacaca taatatgaca tattttacta cataactatt actacaaagt    3540
tatatataac ttttcttct ctgggcttat ataaattttc atatatatac atatataaat     3600
tttatgtata tataatagtt tttgaaaagt agaaaaaaaa tacaattagc caagtgtggt    3660
ggctcacacc tgtaacctta gcactttggg aggccgaggt ggacagatca cttgaggtca    3720
ggagtttaag accagcctgg ccactgtggt gaaaacttgt ctctactaaa aatacaaaaa    3780
ttagccgggt gtggtggcgg gcacctgtaa tccagttact ccagaggctg aggcaggaga    3840
atcgcttgaa cctgggaggc agacgttgca gtgagccaag atcacgctac tgcactccag    3900
cctgggtgac agagcgagac tccatctcaa aaaaatatat atattacata taatacatat    3960
aaatatatat aattatatat ataaatttat tatatatata ataaaataca tatataattt    4020
actagaagat aaattagagt tggttattac tgtcacaaga aaggactgc tttgtttgtt     4080
atttagcccc tgctttggac tggtctcctg ttgaacagag cctggaagag gcttgtgtg     4140
cagttggttt atatggacca tgatcctaga gaagagaagt tgagacaggg gaaagtgaga    4200
cagggaaggc aggaaagcca caaaatgggg gccttctcca gctagtcacc acagtgggca    4260
atggaggctc aatcccatca agcccttcag aggggctgtg tagactgcaa cagaagaggg    4320
gaggtttacg catggatctg ataccctctt ggccaagggc tatcccatgg agtatattgc    4380
gcttccctga tactcagatg tggggacgag gtttgttctt gcagactgat ttttttttt    4440
tttttaagat ggagtctttc tctgtccccc aggctggagt gcggtggcac gatcttggct    4500
cactgcaacc tccgcctcct gggttcaagc aattctcctg cctcagcctc ccgagtagct    4560
gggattacag gtgcacacta ccacgcccag ctaactttg tatttttttt tttttccagt     4620
acagacaggg tttcaccatg ttggccaggc tggtcttgaa ctcctgacct caagtatcca    4680
cccatcttga cctcccaaag tgctgggatt acaggcatga gccacggcgc ctggcctgtt    4740
cttgtagact ttctatgcag aaagtcagag aagctgggcc acggtggctg aggcgaggtc    4800
cccgcaggtg ataactgcaa gaggcaggtt gcctcagcaa tgactgcaaa aaagtgggca    4860
ggatgtgagg ggagggtgag gggagaaacc tgaggtgttc aacacaagtg ctgcagattc    4920
cctttcctca cctagaatag gatggggatg agaatccctc atgggagtca tcatgcaaat    4980
tagcagtcac acagggaagc acccagtgca gcgctgagca gtggccaccc agtgaataaa    5040
atataactag aaaggcttat tttacttgag ttccactatt gttttttgttt ttgttttgt    5100
tttgttttt gaagatggag tctcgctcta tcaccaggct ggagtgcagt ggcgtggtct    5160
tggctcactg caacctccac ctcctggatt caagcaattc tcctgcctca gcctcccaag    5220
tagctgggat tacaggcaca cgccaccatg cccggctaat ttttgtattt ttagtggaga    5280
tggggtttca ccatgttggc caggctggtc ttgaactccc gacctcgtga tccacccgcc    5340
tcagcctccc aaagtgctgg gattacaggc atgagccact gcacctggcc agggttccac    5400
tattgtttta aagcatcatt caataatcaa tatgtcaaca tgtgcataac attttaataa    5460
catgcgttga ttctagagac agtacaagtt agagcagtac tcaggacaat agtctattag    5520
```

```
ctagtcttca ctttcctaag atgtttctga caacctgtag ataattaggc atagcttgtt   5580
ttacttcatt cctttcattt atgtaatatg gactgaactt tccagtgata gaaaatatct   5640
atgaaaatta ttacaatgcc tatgtctaca ggcaaacgag ttaataaatt cagtttccgg   5700
gttgaggtct ctaaaatgcc aagtctataa agaagcgacg gcagagaaca cagaacattt   5760
ccagaatttt gtaatagaca tgaacccttta aaccacagaa ggactgaatt taacatttta   5820
aaaaacctag aaaaaaaaca gctgggcgtg gtggctcacg cctgtaatcc cagcactttg   5880
ggaggctgag gcaggcggat cacgaggtca ggagttcgtg accagcctgg ccaatatggt   5940
aaaaccctgt ctctactaaa aatacaaaaa ttagccaggc gtggtggcag gcacctgtag   6000
tcccagctac tcaggaggct gaggcagaag aatcacttga acccaggagg cagaggttgc   6060
aatgagctga gatcatgcca ctgtactcca gcctgggtga cagagcgaga ccctgtctca   6120
aaaaaaaaaa aacaaaaaaa aaaaccttaa aaaataaaag ccccaaaaat gctaactatc   6180
tgacacagta cagcccttaa tattttcaca gtctcttttt ggttttcctc cacattcaca   6240
atgaaatgtt agtgatttta aaacattcca gagaaatttt agtgttgaca catctttatt   6300
gagggccatt tcatttatag ttacttatgt aatcatccaa acaattcagc tcagcatact   6360
ggggctcaga gaggtggagt catttaccca aagtcacaca gctgggacat ggcagagctg   6420
aactaggagc tatgacttcc ggcttaggtc caggcccctt tacgagattg tttccctgcc   6480
tttgggtttt gcatcctcta ttctgggctt ccacccgcat gccagatggc tctattcctg   6540
gagtctgacc attgccagat gctcctggct gacatgacct agaagaagcc agcaggctca   6600
taacttaacc atcgcccctg ccaaatggga actggccttg ccgtcatcct ggaagccatt   6660
ccctgacatt ttgttttatt gcagttcatg tttattccag ctaatgcaca taaggagtgg   6720
ttcctgcaag gcacaatctg aagggctcct tgctcagagc cgtaagggcc atggtgggat   6780
tcagcaggga acttggcacc agccaggcac ttttgctgcc tcttcttgc cagtgagggt   6840
agaagaactg ataagaggat tgagtgcaca gcccaggagc tgagagttta caaggcaacc   6900
cactgggacc tgagctcagc cccaggagtg ggtcacccca caaagtgctg agcagcatct   6960
ttgagactct tctgaagcct ccagtagcca tctgggtcca gtcgggagat agaaatcaca   7020
cagtgggtta agctggggaa gtttacttta aagaattact aaccgtgatg aaagagcaac   7080
tatagataga cgtgaactcc ataggcacct agggctgagg gagggtgccg gacaagcttg   7140
gaaggggaag gtgaggttca gcacatcagc ttgcagagaa ggtggctaag gtgtgcaggc   7200
ctcagctggt ctgcagctgc aataggccgc ctcccagtgc aggtgaggag ggcaacctgc   7260
aacgtgtggc aagggcatgg tgggagtcag ggcaggcaca ggcaggaggc ctccagagca   7320
ctgaggtccg tgtgcaggga ctctgggttc cttgttggga gggctgtgga aaggttatgg   7380
ccaggctgtg gctgtgaggt cacagaagaa cttcgctctg ggtccgtggc tggggtagga   7440
ctccaacaaa tgtcctcaca gtcataccac ctatggacgc aggacaggaa aactgcagac   7500
cttttcctc ccacgatgtc cctccagcgc cctctactga gatagttcaa catcgcgctc   7560
acttcaaagc tcttgttctt cagacagcat acatgggagg gtgcattcag ctctgagagg   7620
caatgcgttt ataactgaca cacctcctca gcacaggatg gaaagagttcg cagctgccat   7680
ggcctcggaa gacatggggtt caagtcccag cgataccact tagctgtgtg accttgggca   7740
tgttacttaa cctctctgaa cctcggtttc ctcatttgca aaggggata ttaatgttca   7800
ctttcaggac cattatttga aagtagtgag tagcaagcac ccagcacagt actggctcat   7860
aagagacact taataagtag tagcgatagt tcaactttat caggcgctat ctgcagtcct   7920
```

```
aaagcctttc tctatttctc tgaaactttg aaggcaccag atcacattta aaaattacat    7980
aaaaattact tgaaatgggc aaagagctat aaatgccgac aaaccatctt gtttcacaaa    8040
aaaaaaaaaa aaaaaagctg ttttttagag ttgcaaagcc agtacatact ttagctatcc    8100
acaaggaagt catctgtgaa aatgcctgac ttttttgggt ttcactttct tccttccctc    8160
tatagcaaaa ggggcatttc tttcttaatt ttctccccac tgactggtag gtaggtaccc    8220
ctactttcct tagtatacat cttttctcgg taagttgtta aattaaataa ccagcataaa    8280
atacatcatt ttgtatgtgt aaggggcca gatgcagggg agggatggct cgcctgaatt     8340
taatatttt ttaaaaacct aaaaaaaaaa gccctaaaaa tgttaacgat ctgtcacaat    8400
atagccctta atattttcat aatctctttt tggttttctt ccacattcag aatgaaatgt    8460
tagtgatttt gaaacattcc agagaaattt tagtattgac acatttatta agggaccctc    8520
ccatggcaac tgtggatggc atagctgaag tgtagggaca aggttggggc agtcctccag    8580
actttgtgta cagatggcat gcagtatttc tctctcctca cattgcctga aaccaactcc    8640
tttttttttt tttttttttt tttttgagac agagtctctc tgtcacccag gctggagtcc    8700
aatggcacaa tctcagctca ctgcaacctt gcctcccag gttcaaacga ttctcctgac    8760
ttagcctccc tagttgctga gattacaggc atgtgccact atgcccggct aattttgta    8820
tttttagtag agacagggtt tcagcatgtt ggtcaggctg gtctcgaact cctgacctca    8880
tgatccaccc acctcagcct cccaaagtgc tggaattaca ggcgtgagcc accatgccca    8940
gcaactctta tattctgaga gttgagacaa tgaaagaaaa gaaatttgag ttgtcctgag    9000
gcagagtctg cagtgatcca agaagaggta cagatgaaag gaaaccagct caattcaagg    9060
aacttgctta atgccctgat tttgaaaaat tgtcctggca agactttgcc acatcgaatg    9120
agcctctgca cattgcagga ggctggcagg gccaggag ggtgggctgc tcctaacagc      9180
ctgggtgtgt gttctgggcc taagagagaa ggcatggcaa tcggcgaggc agcatcagag    9240
aggaaggtta cagatggttc tgccaccgt gtacaggaag gcggtcactc tctcttacct     9300
ctccctggca gcacagaaga acagggaacc tcgggcaccc tgtccctctc ccccataggc    9360
agcaccaagt ccctgccgga ggtgtgtgtt gcctgcacag ggggagaagg gaagcagctg    9420
gtactggtct caggtcgatc taaggaaact ccatttgacc tagtgaatca gtccctgccc    9480
tggataccct cctaggccaa tgcaacctt agaatgaaga acaaagggt ttcctcaccc      9540
ctgcacaacc tcagataggg agaaggagac gcagggaatg aaataaaagt ttccaggact    9600
ctccaggagc cattcagatt gtccaagaaa ctggtttccg cagcagcctg gaataaaccc    9660
attttccttc tcgggtatga ggactttgcc agattatgat ttccttaagg gcatggactg    9720
attgtgtctt tttttttttt ttttaaaca tagactagcc tattagacaa acttgtgtct    9780
tagacacctt tttttcttga gcacctagca cagccttgca ctcaataggt gctccaatga    9840
tgtgactaaa aggatggata aatagctctg tggatttgag gctaggaata atgaaggcct    9900
gccatgtccc gggggtact cccaattgcc cctggagttt ggaatgcaca ttgaggatgt     9960
cctcagttac atatacattt tggcttatga gtctttcttt ttttaatttt tttttttttt   10020
aagacagggt ctcactctgt cacccagact ggagtgcagt ggcatgatca tggctcactg   10080
cagccttgcc ctcttggact caagagtcat cttcctgcct cagcctcccg agtagctgag   10140
accacagact gcaccaccac acccagctaa ctctttaatt ttttgtaaag atggggtctc   10200
gctatgttgc ccagcctggt cccaaactct tggcctcatg caatcctgcc acctcggcct   10260
cccaaagtgc tgggtttaca ggcatgagcc actgcgcctg gccagcttat gggttttaac   10320
```

```
tacttacatg gtgcactcta gactgaggga tatcccaggg atggaggacc cacccacctc    10380
cagggcatta acacttttag ggaggctaac aactgcagcc acacagaggc agggtggag     10440 aggagagaag ggtagctggg atcagggca ggcagctgca gcagctactg agctggctca    10500
ctgtgggcag catggctgtc tggcccagcc tgcacctgag agctagctga atgttttctt    10560
cacctccttc cagggagaaa tttttccag tactataatt tgttgaagct gaaccccagc    10620
aactcaaaca aggtaccctg actctggaga tgtgaaaatg taaaataatg tgtggctttg    10680
atgaaatgtg gtagaaccag aggattaaga cttctgtggt gatcctctct gcctgaaatc    10740
taaatttagg agagctgagc aaacaaatga tcaaaggcag aacatgtctt cccgaccctc    10800
tcggctgtgt aggcgctccg gcctcagggg atgcactgac tttcctccca ctgtcctgaa    10860
cacctgagaa tcctgagcgg ggaacaagtt gctcaaaggg cagagaagtg actcagaggt    10920
tcagcaagag aaaagcccag tgtattaagc atgtcttttt attctgatgc tttgctgtct    10980
gggccttgca aacgtgagag ggactgcccc tcccaggggt agccagttcc tacggttagc    11040
aaaggactca cctgggagga cagctttcat atgcaaacca accaatccag agcccacacc    11100
ctgtgaccac ctccatctgg ctcaaactca aggccactgt cccctgacc taatcaccca    11160 gggcctggta ccagacaatt agagataact cctgtgaccc cagatcctgc tgaaattatt    11220
caaactcccc aatcctaaac ctgcttaccc tgcctcccct ttctttcctt cccatggaaa    11280
gaataaaggc gctttcccac attttcccct ggtgccctct tctggagcaa ccctggtgct    11340
tccccaggtg gcctcctggg cttagtgtgc ccccttcctc ttgggctctg tgagtacaac    11400
aacttgtaaa gataattttt ttttagagca gttttatgtt cacagccaaa ttgagagaaa    11460
agtacaaaca gttcccagat actactggcc cccacacatg cacagcctcc ccgattatca    11520
tcatctcccg ccacagcagt tgttacaact gatgaacctg catcagcacg cacaacaccc    11580
aaggtccacg gtttaaatta gggttcattt ttggtgttgc gccttctatg ggtttagaca    11640
aatgcatagt gacatgtgtc caccattata gtatcataca cagtattcat tgccctaaaa    11700
atcgtctgtg cctcacctag tcatcccttc ctcacccaac aactgctgat cttttactg     11760 tctccataat tttgctttaa cttgcttttc agtgacaatt gcctcctggg atgttggcct    11820
tgccacacct gaataatcat caaacctgca ttttatttgt ttttatgtgt atgtgatggg    11880
ttttttggga ggttggaggg gaggacaggg tctcactcta cgccagggct ggagtgcaga    11940
ggtacgatca ctgctcacca cagccttgac ctcccggtct caagtgatcc tcccacctca    12000
gcctcccaag tagctgggac tgcaggtaca catcaccacc caggctaact ttttgtagtt    12060
tttgtagaga tgggatttca ccatgttgcc caggtttgtc ttgaactcct gggctccagt    12120
gatctgtcta ccttggcttc ccaaagtgct gggattacag gtatgagcca ctgggcctgg    12180
ccaaactgca ttttaaaata gccaagcctg ttccttgtga ctattgcctc atccttgtat    12240
tcaagactgc tgtaagatca taatcctaag caagagtaga gacatgtagc acaccatgat    12300
cacttactgt ctaaccaatg ctgcccaccc gcttcccttc tgtatggctc accccccca    12360 ccccaaactc ctataggaac tctgcacaca ctccctctcc attatgcaaa actggtctca    12420
gaaaggaatc agacagaata tttctactga aagtataaag cttaatatgt tacttcttac    12480
aagaatattt gcatataaca agggaaaaaa ccttaagtca tgcagtaaac ttttatcttt    12540
tttttttttt taacaggagt ctccctatgt tgcccaagct ggtcttgaac acctgggctc    12600
aagtactcct cctgtcttgg cctcccaaag tgctgggatt acagacatga gccacacttc    12660
tttttttttt ttttttttttt tttttttctt gagacagagt cttgctctgt tgcccagact    12720
```

```
ggagtacagt tgcacaatcc cggctccctg caacctttgc ctcctgggtt caagtgatcc    12780
tcaacctcct gagtatctgg aactacaggc atgtgccacc acaccctgct aattcttgta    12840
tttctagtaa agatggaatt tcaccacgct ggccaggcta gtcttgaact cctggcctta    12900
agtgatccgc ctgcctcggc ctcccaaagt gctgggattt cagtgtgagc cactgtgccc    12960
ggtctctttt tttttttttt tgagaccttg agaccgggcc ttgctctgtt acccaagctg    13020
gagtgcagtg gcaggatcat agctcactgc agccttgaac ttctgggctc aagcaatcct    13080
cccacatcag cctcccaagt acctaggact gcagatgctt accaccatgc ccagctaatt    13140
tttcatgaat ttttaattat tgaaattcag acatctaaga agatgctgag gactgtctcc    13200
atattcctga aattacgact cacctattca caaaccagcc cttctagtgg aattaaaata    13260
ttatttgatt ttgaataccc tactctaagg taggcacatt gccctgcaat ttattattta    13320
tgaggttttt aattatggaa ttgttcaaat attcacaaaa gtagagagac tacaatgaac    13380
tccaatgtag ccatcactca ggcccaactg ttatcagcac agtccaatca tgttttatct    13440
tcccttctct gacccccaac ccatcccag tccttatcta aaatcaaatc tcaaacacca    13500
tatctttggg agcctattta tttagttagt tagttttcag acagagtttc tttcttgttg    13560
cccaagctgg agtacaatag tgtagtctcg gctcacagca atctccccct ccttggttca    13620
agcaattctc ctgcctcagt ctcccaagaa gctgggatta taggcacctg ccaccacatc    13680
cagctaattc ttttgtgttt ttagcaaaga cagggtttca ccatgttggc caggctggtc    13740
tcgaactcct gacctcaggt gatccgcctg cctcggcctc ccaaagtgct gggattacag    13800
gcatgagcca ccacgcctgg ccggcagcct atttaaatgt catcctcaac atagtcaatc    13860
cttgggccat tttttcttac agtaaaattt tgtctctttc ttttaatgca gtttctacgt    13920
ggaatttgga cactttggcc ttccaggaac tgaagtccga gctaactgaa gttcctgctt    13980
cccgaatttt gaaggagagc ccatctggct atctcaggag tggagaggga gacaccggta    14040
tgaagttaag tttcttccct tttgtgccca cgtggtcttt attcatgtct agtgctgtgt    14100
tcagagaatc agtatagggt aaatgcccac ccaagggga aattaacttc cctgggagca    14160
gagggagggg aggagaagag gaacagaact ctctctctct ctctgttccc ttgtcagagc    14220
aggtctgcag gagtcagcct ttccctaaca aagccctcta tcctatcacc cacacttggg    14280
aggctgggct gggctgcaca gggcaagatg agagatgtgt tgatttcatc cacttgattg    14340
tcatgtagaa ttagatatac ttgagaagtt acattttca gtagcgcctt catatcttta    14400
ttttagggac aggtatacac caagcaccat ctcagccaca atctgttact aacagtatgt    14460
tttctgaact ttggccactt aggaaaagta cagtttggct ctctccaaag tgttccctga    14520
aagtccaact ttatgactaa tactgtgatt tccagaaact ttgactatcc atgttattga    14580
caatgattac tagcactgaa gggcatgcat gcaagtaggg gttatgaaat atttaaaaca    14640
cggttctcta agatatgagc agcaaagtgt ttctaccttc tatgagggaa ccgaaggtgc    14700
cattaaaagt agagaaatct ggaccaggca tggtggctca gcctgtaat cccagcactt    14760 tgggaggctg aggcgggcgg atcacttgag gtcaggagtt caagaccagc ctggccaaca    14820
tggtgaaaca ctgtctctac taaaaataca aaaattagcc aggcatggtg gcagtcatct    14880
gtaatcccag ctacttggga ggctgaggca ggaaaattgc ttgaacccag gaggcagagg    14940
ttgcagtgag ccgagatcac accactgccc tccagcctgg gcgacagagt gagactctgt    15000
ctcaaaaaaa aaaaaaatac agacatctgt tgtgattctg gtaactctaa attttcaacc    15060
gtctcttcac tacatttaaa aaattatttt ctaaaccaaa ttagccaggt gtggtagcag    15120
```

```
gcacctgtag tcccagcaac tcaggaggct gagatgggag gggtgcttga gcctggaagg    15180
tcgaggctgc agtgcactgt gattgcacca ctgcactcca gcctaggtaa cagtgcaaga    15240
ccctgtctca aaaataatt attttcatgt ttattatatt aaaatgatgt atgaaatatg    15300
tgactcatca gggcttgaaa aactttgttg tatggagatt attcttatga gttgattttt    15360
ctctctccta ccttatagta atgaaataaa ccaggcatga aagtcacaat aagtaataca    15420
atgaacaccc atgggtccct gcccagctta agtagaatat tacaaatgca gttgaagccc    15480
tctgtgcaac tttcatcctt acaactgata ctgagtgaat tgtactttaa atattttata    15540
gctcccactc ccatgcatgc ccctcagtga tagcaataat tgtcaataac atgaaacaca    15600
gattgatcat atagcattta ccatatattt actctatacc aagcacttaa catatataat    15660
tacatttaaa atttacaaca gccctactac ccaaaacact attagtatcc ccttttacaa    15720
atgcgataac tgaggcgtag agagctaagt aacttactga aagtcacaca gccagcgggt    15780
ggtagagcct agctttaaac ccagacgatt tgtctccagg gctgtcacat ctactggctc    15840
tgccaagctt ccgcatgatc attgtctgtg tttggaaaga ttatggatta agtggtgctt    15900
cgttttcttt tctgaattta ccaggatgtg gagaactagt ttgggtagga gagcctctca    15960
cgctgagaac agcagaaaca attactggca agtatggtgt gtggatgcga gaccccaagc    16020
ccacctaccc ctacacccag gagaccacgt ggagaatcga cacagttggc acggatgtcc    16080
gccaggtttt tgagtatgac ctcatcagcc agtttatgca gggctaccct tctaaggttc    16140
acatactgcc taggccactg gaaagcacgg gtgctgtggt gtactcgggg agcctctatt    16200
tccagggcgc tgagtccaga actgtcataa gatatgagct gaataccgag acagtgaagg    16260
ctgagaagga aatccctgga gctggctacc acggacagtt cccgtattct tggggtggct    16320
acacggacat tgacttggct gtggatgaag caggcctctg ggtcatttac agcaccgatg    16380
aggccaaagg tgccattgtc ctctccaaac tgaacccaga gaatctggaa ctcgaacaaa    16440
cctgggagac aaacatccgt aagcagtcag tcgccaatgc cttcatcatc tgtggcacct    16500
tgtacaccgt cagcagctac acctcagcag atgctaccgt caactttgct tatgacacag    16560
gcacaggtat cagcaagacc ctgaccatcc cattcaagaa ccgctataag tacagcagca    16620
tgattgacta caacccctg gagaagaagc tctttgcctg ggacaacttg aacatggtca    16680
cttatgacat caagctctcc aagatgtgaa aagcctccaa gctgtacagg caatggcaga    16740
aggagatgct cagggctcct gggggagca ggctgaaggg agagccagcc agccagggcc    16800
caggcagctt tgactgcttt ccaagttttc attaatccag aaggatgaac atggtcacca    16860
tctaactatt caggaattgt agtctgaggg cgtagacaat ttcatataat aaatatcctt    16920
tatcttctgt cagcatttat gggatgttta atgacatagt tcaagttttc ttgtgatttg    16980
gggcaaaagc tgtaaggcat aatagtttct tcctgaaaac cattgctctt gcatgttaca    17040
tggttaccac aagccacaat aaaaagcata acttctaaag gaagcagaat agctcctctg    17100
gccagcatcg aatataagta agatgcattt actacagttg gcttctaatg cttcagatag    17160
aatacagttg ggtctcacat aacccttac attgtgaaat aaaattttct tacccaa      17217
```

METHOD AND APPARATUS FOR PREVENTING NEURODEGENERATION

CROSS-REFERENCE TO RELATED APPLICATIONS

This application is a continuation of U.S. application Ser. No. 12/563,483, filed Sep. 21, 2009, now U.S. Pat. No. 9,789,336, which is a continuation-in-part of U.S. application Ser. No. 11/409,067, now abandoned, filed Apr. 24, 2006, which claims priority to U.S. Provisional Application No. 60/674,311, filed Apr. 25, 2005. The entire disclosure and contents of these two applications is incorporated herein by reference in their entirety.

GOVERNMENT INTEREST STATEMENT

United States government may own rights to the present invention as work done in development of the invention described herein was funded in whole or in part by Federal Grant No. F32-Ey14515 from the National Institutes of Health.

FIELD OF THE INVENTION

The present invention relates generally to a method for preventing neurodegeneration, and specifically to a method of preventing, e.g., protectively inhibiting neurodegeneration that occurs in the eye, particularly a condition known as glaucoma. The method of the invention also generally relates to the use of high-dose ionizing radiation, such as ionizing radiation including gamma radiation and x-ray radiation, beta and proton radiation, and bone marrow transfer, or both in the treatment of neurodegeneration, and particularly a form of neurodegeneration of the eye known as glaucoma, such as a hereditary form of glaucoma.

BACKGROUND

The glaucomas are a group of complex neurodegenerative diseases. As a consequence of this neurodegeneration, glaucoma patients exhibit a loss of retinal ganglion cells (RGCs), characteristic changes in the visual field, and degeneration of the optic nerve (Ritch, R., et al. (1996)[1], and Weinreb & Khaw, (2004)[2]. Glaucoma is traditionally viewed as a pressure-induced neurodegeneration, in which deleteriously high intraocular pressure (IOP) results in optic nerve damage over time. As a consequence, all major existing glaucoma therapeutics aim to lower IOP. However, many individuals who have high IOP for extended periods do not develop optic nerve and retinal damage, whereas others develop optic nerve damage despite normal IOP values (Heijl, A., et al. (2002)[3], Collaborative Normal-Tension Glaucoma Study Group (1998)[4]. Thus, glaucoma is defined as a neurodegeneration and magnitude of IOP may not indicate current or future glaucoma status. Therefore, treatments that directly target the retina and optic nerve need to be developed.

Mouse studies are very useful for studying mechanisms contributing to multifactorial diseases and for testing potential treatments; see John, S. W., et al. (1999)[5]. DBA/2J mice are a naturally occurring mouse model of glaucoma. DBA/2J mice develop an age-related form of hereditary glaucoma initiated by mutations in two genes, Tyrp1 and Gpnmb; see John, S. W. M., Smith, et al. (1998)[6], Chang, B., et al. (1999)[7], and Anderson, M. G., et al. (2002)[8]. Clinically, indications of DBA/2J glaucoma are first evident by a pigment-dispersing iris disease that involves melanosomal and inflammatory components. As dispersed pigment from the iris disease accumulates within the aqueous humor drainage sites, DBA/2J mice develop an elevated IOP, which progressively insults RGCs and the optic nerve. By 10 to 12 months, the majority of DBA/2J mice have severe glaucoma evident by massive RGC loss and optic nerve damage.

Little is known about the mechanisms or molecular pathways that contribute to RGC degeneration in the glaucomas. As in other neurodegenerative diseases, the majority of effort has focused on apoptotic degeneration pathways; see Quigley, H. A. (1999)[9], and Nickells, R. W. (2004)[10]. Recently, there has been recognition that distinct degenerative processes exist within different parts of a neuron, see Raff, M. C., et al. (2002)[11].

Bone marrow transplantation combined with radiation or chemotherapy is used in the field of clinical oncology where it is used for Non-Hodgkins Lymphoma, Hodgkins Disease, breast cancer, and some types of leukemia and testicular cancer. Intense immunosuppressive conditioning combined with autologous hematopoietic stem cell transplantation is reported to treat autoimmune diseases such as multiple schlerosis (MS) and lupus, see Robert A. Good (July 2000)[12].

The above review demonstrates a need continues to exist in the medical arts for more effective methods of treating and inhibiting the progression of neurodegeneration that accompanies the forms of glaucoma.

SUMMARY

The above and other long felt needs in the art are met in the present invention.

According to a first broad aspect of the present invention, there is provided a method for treating, inhibiting and/or preventing neurodegeneration, comprising: administering a treatment regimen comprising administering radiation in a neurodegeneration-inhibiting amount to a head or eye area of a subject having a potential for developing glaucoma, to thereby protectively inhibit the eye of the subject against neurodegeneration caused by glaucoma, prior to the onset of any indication of glaucoma.

According to another broad aspect of the present invention, there is provided a method for treating, inhibiting and/or preventing neurodegeneration, comprising: administering a treatment regimen comprising radiation to an area of interest in an animal, wherein said radiation is administered in a neurodegeneration-inhibiting amount, and administering an effective amount of bone marrow cells. In some embodiments, the bone marrow is an autologous bone marrow sample. In other embodiments, the radiation is administered at the same time or before the bone marrow is administered.

According to another broad aspect of the present invention, there is provided a method for treating, inhibiting and/or preventing neurodegeneration, comprising: administering a treatment regimen comprising administering radiation in a neurodegeneration-inhibiting amount to a head or eye area of a subject being a suspect of developing glaucoma manifestations, to thereby protectively inhibit the eye of the subject against neurodegeneration caused by glaucoma, prior to the onset of glaucoma.

According to another broad aspect of the present invention, there is provided a method for treating, inhibiting and/or preventing neurodegeneration, comprising: administering a treatment regimen comprising administering radiation in a neurodegeneration-inhibiting amount to a head or eye area of a subject being a suspect of developing glaucoma manifestations, to thereby protectively inhibit the eye of the subject against neurodegeneration caused by glaucoma, prior to the onset of glaucoma and not requiring the need to reduce the IOP of the subject.

According to another broad aspect of the present invention, there is provided a method for treating, inhibiting and/or preventing neurodegeneration, comprising: administering a treatment regimen comprising administering radiation in a neurodegeneration-inhibiting amount to a head or eye area of a subject having glaucoma, to thereby further inhibit the eye of the subject against neurodegeneration caused by glaucoma, wherein radiation is delivered to the subject prior to an incision to the eye.

According to another broad aspect of the present invention, there is provided a method for treating, inhibiting and/or preventing neurodegeneration, comprising: administering a treatment regimen comprising administering radiation in a neurodegeneration-inhibiting amount to an optic nerve head of a subject having glaucoma, to thereby further inhibit the eye of the subject against neurodegeneration caused by glaucoma, wherein radiation in a neurodegeneration-inhibiting amount interacts with the optic nerve head.

According to another broad aspect of the present invention, there is provided a method for treating, inhibiting and/or preventing neurodegeneration, comprising: administering a treatment regimen comprising administering radiation in a neurodegeneration-inhibiting amount to an optic nerve as it exits the eye of a subject having glaucoma, to thereby further inhibit the eye of the subject against neurodegeneration caused by glaucoma, wherein radiation in a neurodegeneration-inhibiting amount interacts with the optic nerve as it exits the eye.

According to another broad aspect of the present invention, there is provided a method for treating, inhibiting and/or preventing neurodegeneration, comprising: administering a treatment regimen comprising administering radiation in a neurodegeneration-inhibiting amount to a retina of a subject having glaucoma, to thereby further inhibit the eye of the subject against neurodegeneration caused by glaucoma, wherein radiation in a neurodegeneration-inhibiting amount interacts with the retina.

According to another broad aspect of the present invention, there is provided a method for treating, inhibiting and/or preventing neurodegeneration, comprising: administering a treatment regimen comprising administering radiation in a neurodegeneration-inhibiting amount to myelin junction region of the optic nerve of a subject having glaucoma, to thereby further inhibit the eye of the subject against neurodegeneration caused by glaucoma, wherein radiation in a neurodegeneration-inhibiting amount interacts with the myelin junction region of the optic nerve.

According to another broad aspect of the present invention, there is provided a method for treating, inhibiting and/or preventing neurodegeneration, comprising: administering a treatment regimen comprising administering radiation in a neurodegeneration-inhibiting amount to retina and optic nerve head of a subject having glaucoma, to thereby further inhibit the eye of the subject against neurodegeneration caused by glaucoma, wherein radiation in a neurodegeneration-inhibiting amount interacts with the retina and optic nerve head.

According to another broad aspect of the present invention, there is provided a method for treating, inhibiting and/or preventing neurodegeneration, comprising: administering a treatment regimen comprising administering radiation in a neurodegeneration-inhibiting amount to the optic nerve head and myelin junction region of the optic nerve of a subject having glaucoma, to thereby further inhibit the eye of the subject against neurodegeneration caused by glaucoma, wherein radiation in a neurodegeneration-inhibiting amount interacts with the optic nerve head myelin junction region of the optic nerve.

According to another broad aspect of the present invention, there is provided a method for treating, inhibiting and/or preventing neurodegeneration, comprising: administering a treatment regimen comprising administering radiation in a neurodegeneration-inhibiting amount to the retina, optic nerve head and myelin junction region of the optic nerve of a subject having glaucoma, to thereby further inhibit the eye of the subject against neurodegeneration caused by glaucoma, wherein radiation in a neurodegeneration-inhibiting amount interacts with the retina, optic nerve head myelin junction region of the optic nerve.

In some embodiments, the invention provides for a method that provides for the treatment of an area of an animal with radiation at other than over an entire body (whole body). For example, the area of the body to be treated may in some embodiments be the head area. In even more specific embodiments the head area is further defined as the eye area of the head. Even more specifically, the eye area may be further defined as the eye itself, the area may be further defined to the posterior section of the eye. In this manner, a treatment of radiation may be focused at the area of the body directly of interest for treatment, such as that area of the body that is afflicted with a degenerative disease or suspected to be afflicted with a condition of interest to be treated. This method also permits the ability to avoid radiation exposure to areas of the body that are not expected to be afflicted with a condition of interest to be treated. Among other advantages, this permits a reduction in dose inhomogeneity in the radiation treatment being administered to an animal. In addition, this procedure of administering the treatment of radiation to a specific area rather than the entire body of an animal will reduce and/or eliminate damage to healthy tissue that is not the target of the therapy.

In some embodiments, the method provides for a treatment regimen comprising radiation that is gamma radiation. In some embodiments, the treatment regimen comprises a single dose of radiation. In some of these embodiments, the radiation is administered to an area of the body at an amount of radiation comprising from about 1 Gy to about 15 Gy, preferably in a range comprising from about 5 Gy to about 10 Gy.

In other embodiments, the treatment regimen comprises more than a single dose of radiation, such as two approximately equal doses of radiation, or as multiple doses of radiation.

In particular embodiments, the treatment regimen comprises two doses of radiation, particularly two approximately equal doses of radiation. In some of these embodiments, the dose regimen will comprise an initial and/or first dose of radiation comprising from about 5 Gy to about 7 Gy, and a subsequent and/or second dose of radiation comprising from about 5 Gy to about 7 Gy. In some embodiments, the dose regimen will comprise an initial and/or first dose of radiation comprising about 5 Gy and a subsequent and/or second dose of radiation comprising about 5 Gy.

In other embodiments, the treatment regimen comprises multiple doses of radiation, given over an appropriate and/or prescribed period of time. In these embodiments, the treatment regimen may comprise a regimen in which radiation is administered in fractions and/or multiple treatments of radiation at doses in a range comprising about 1.0 Gy to about 5.0 Gy. In some embodiments, each of the multiple doses of radiation comprises a radiation dose comprising about 2.5 Gy.

In some embodiments, the administration of the radiation is by brachytherapy, a procedure in which the radioactive material is sealed in needles, seeds, wires, or catheters. According to some embodiments, the brachytherapy delivery mode selected is placed in relatively close proximity to the area to be treated, such as the head, ocular or eye region. With bracheotherapy, the median dose of radiation that will be delivered to a specific area to be treated will be at a dose of about 1 Gy to about 15 Gy, preferably in the range of about 5 Gy to about 10 Gy.

An alternative method is via external beam radiotherapy that will be delivered to specific area of treatment at a dose in a radiation range comprising about 1 Gy to about 15 Gy, or in a radiation range comprising about 5 Gy to about 10 Gy.

With either or any of the particular treatment approaches presented herein, radiation is intended to be focused in the head and/or ocular region.

In some embodiments, the invention provides for a method that is directed to a method of treating, inhibiting and/or preventing neurodegeneration of the eye. In some embodiments, the neurodegenerative condition of the eye is glaucoma, particularly age-related forms of glaucoma, including those associated with particular genetic profiles, including those that are characterized by the presence of and/or initiated by a mutation in the gene Tyrp1, Gpnmb, or a mutation in the Tyrp1 gene and the Gpnmb gene, such as in DBA/2J mice.

According to yet another aspect of the present invention there is provided a method of characterizing pathways necessary for glaucoma induced retinal ganglion cell degeneration comprising treating an area of an animal, for example, an area of a DBA/2J mouse, with radiation.

According to another aspect of the present invention, there is provided a method of characterizing a physiological and/or molecular event of interest associated with glaucoma induced retinal ganglion cell degeneration in an animal. In one embodiment, the method comprises measuring the particular physiological and/or molecular event of interest in an animal having glaucoma or with a predisposition to glaucoma both before and after treatment (or alternatively treated group vs. untreated group) with a neurodegeneration-inhibiting amount of radiation and/or bone marrow, and comparing said before and after measures of the physiological and/or molecular event of interest. In the method, differences may be identified between the before and after measurements (or alternatively treated group vs. untreated group) with of the physiological and/or molecular event of interest. By performing this kind of comparison, defined changes in measures of a specific physiological and/or molecular event of interest may be examined in order to further characterize the mechanism/s by which radiation and/or bone marrow treatment elicits a neurodegenerative protective effects in an animal having glaucoma or predisposed to induced retinal ganglion cell degeneration.

According to another aspect of the present invention, there is provided a method of characterizing a physiological and/or molecular event of interest associated with the application of a neurodegeneration-inhibiting amount of radiation to glaucoma induced retinal ganglion cell degeneration in an animal. In one embodiment, the method comprises measuring the particular physiological and/or molecular event of interest in an animal having glaucoma or with a predisposition to glaucoma both before and after treatment (or alternatively treated group vs. untreated group) with a neurodegeneration-inhibiting amount of radiation and/or bone marrow, and comparing said before and after measures of the physiological and/or molecular event of interest. In the method, differences may be identified between the before and after measurements (or alternatively treated group vs. untreated group) with of the physiological and/or molecular event of interest. By performing this kind of comparison, defined changes in measures of a specific physiological and/or molecular event of interest may be examined in order to further characterize the mechanism/s by which radiation and/or bone marrow treatment elicits a neurodegenerative protective effects in an animal having or predisposed to glaucoma induced retinal ganglion cell degeneration.

Alternatively, another embodiment of the method may comprise the use of this model to compare the herein described radiation and/or bone marrow treatment for glaucoma induced retinal ganglion cell degeneration, with other potential treatments and/or regimens of treatment. In this manner, physiological functions, molecular pathways, protein expression, cellular regulatory regulation or regulatory cell activity, and gene expression patterns, etc., may be compared and used to design comparable and/or alternative or supplementary treatment protocols for pressure-induced retinal ganglion cell degeneration and conditions related and/or associated therewith, such as glaucoma.

By way of example, an animal model that may be used in these methods that develop pressure induced retinal ganglion cell degeneration is the DBA/2J mouse.

The methods of the invention provide for the treatment, inhibition and/or prevention of a disease of interest in any animal, including a mouse, human, dog, cat, horse, rabbit or other domestic or non-domesticated animal of interest. In some embodiments, the animal to be treated is a human.

The present invention provides a method for preventing, inhibiting and/or treating neurodegeneration in an animal having or likely to develop a neurodegenerative disease. By way of example, such a form of neurodegeneration is the neurodegeneration of the eye, including but not limited to inherited and/or age-related forms of glaucoma.

In some embodiments, the animal is a mouse, horse, cat, dog, bird, or other animal, including a human.

While glaucoma is the degenerative disease discussed in detail in the present application, the method is applicable to treat, inhibit, ameliorate, prevent, etc., other degenerative diseases. By way of example, these diseases include, but are not limited to, age-related macular degeneration (AMD), retinal degeneration, optic nerve atrophy, multiple sclerosis, diabetic retinopathy, Alzheimer's disease, Parkinson's disease, stroke, or other conditions following a transient ischemic event, etc.

In some aspects, the present invention provides a method for treating, inhibiting, and/or preventing neurodegeneration comprising administering a treatment regimen comprising radiation in a neurodegeneration-inhibiting amount to an area of interest of an animal. In some embodiments, the form of neurodegeneration that is to be treated, inhibited and/or prevented is neurodegeneration of the eye. In a particular embodiment, the neurodegeneration of the eye is described as glaucoma, particularly age-related forms of glaucoma and/or hereditary forms of glaucoma.

In some embodiments, the methods of the invention provide for administering a treatment regimen to an area of interest of an animal, such as the head area, particularly the eye area. In other embodiments, the methods of the invention provide for administering a treatment regimen to the whole body.

In some embodiments, the method provides a method for treating, inhibiting, and/or preventing neurodegeneration comprising administering a treatment regimen comprising administering radiation in a neurodegeneration-inhibiting amount to the whole body of an animal, and an effective amount of bone marrow cells. In some embodiments, the neurodegeneration-inhibiting amount of radiation comprises a high-dose whole-body radiation. The radiation treatment may be administered before, after, or at the same time that the bone marrow cells are administered to the animal. In some embodiments, the method comprises a first step of administering radiation, and a subsequent step of injecting with bone marrow cells. The subsequent step may comprise any administering step that occurs after an initial step of administering radiation. Hence, the step of administering bone marrow cells may comprise, for example, a second, third, fourth and/or fifth step of the protocol. The sequence of steps in this regard is not critical where at least an initial and/or first step of administering radiation occurs.

In some embodiments of the method, the animal will undergo a syngeneic bone marrow transfer. The term "syngeneic" is defined as a bone marrow sample that has been harvested for treatment which is of a genotype that is the same as that of the animal being treated.

The bone marrow transplantation and/or treatment may be heterologous (harvested from an animal other than the animal being treated) or autologous (harvested from the animal being treated) relative to the animal receiving the bone marrow as defined in the practice of the present invention. By way of example, in humans, autologous bone marrow transplantation is preferred.

The animal will preferably undergo autologous bone marrow transplantation which involves using the subject's own bone marrow. In this instance, the bone marrow is to be harvested prior to the administration of a first or initial treatment with radiation, such as a high-dose radiation, and this bone marrow is then re-administered to the animal in order to re-establish hematopoietic cell function after the administration of radiation. The hematopoietic stem cells for re-infusion into the subject preferably come from the subject's bone marrow. Alternatively, peripheral blood may also be used.

In a preferred embodiment, a bone marrow treatment will be conditioned by the selective removal of T-cells prior to re-infusion into the animal being treated. By way of example, T-cells may be removed using techniques known by those of skill in the art, such as by using antibodies and cell sorting by flow cytometry prior to re-infusion. (Mackall C L, et al. (1997)[1]; Etienne Roux, et al. (1996)[16]; Champlin R., (1990)[17]; O'Reilly R J (1992)[1]; Martin P J, et al. (1985)[19]; Prentice, H. G., et al. (1982)[20]; Waldmann H, et al. (1984)[21]; Antin J H, et al. (1991)[22]; De Witte T, et al. (1986)[23]; Maraninchi D, et al. (1988)[24]; Soiffer R J, et al., (1992)[25]; Filipovich A H, et al. (1990)[26]; Wagner J E, et al. (1990)[27]; Herve P, et al., (1985)[28]).

Techniques for treating humans with selected body section radiation treatment are known in the art. For example, brachytherapy is a focused radiation administration approach that provides for the delivery of a radiation dose to a desired area using radiation that has been sealed in needles, seeds, wires or catheters, and then being placed directly into or near the area of the body where delivery of the radiation is desired. (See L. Lumbroso-Le Rouic et al (2004)[41]).

In the present invention, the method for preventing and treating neurodegenerative diseases includes whole body radiation, or irradiation of a part of the body, of an animal subject by irradiating the subject or subject area with either a single dose of about 10 Grays (Gy) administered to the midplane and about 8 Gy administered to the lungs or, alternately, in fractions of 12 Gy on three consecutive days and 9 Gy to the lungs prior to the bone marrow transplantation. Techniques for treating humans with whole body radiation are known for treating cancer and autoimmune diseases (Belkacemi Y, et al. (1998)[29]; Richard K. Burt, et al. (1998)[30]; Homing S J, et al. (1994)[31]).

In one aspect, the invention provides a method that targets axonal and somal pathways of a neuron. The present methods are profoundly neuroprotective, and can completely prevent detectable glaucomatous degeneration of both the neuronal soma and axons. Because glaucoma observed in DBA/2J mice is known to affect axons and somas, treating an animal afflicted with glaucoma or an ocular degenerative disease like glaucoma, offers a powerful system for determining mechanisms of neurodegeneration and providing neuroprotective treatments.

In some embodiments, the method of the present invention includes irradiating an animal with 1,000 Rads (10 Gy) of radiation in two equal doses. By way of example, the treatment with the radiation may be to the whole body, or instead focused at a desired body area, such as the head area or ocular (eye area). Subsequent to at least one radiation treatment, such as after a second radiation dose, the animal may also receive a bone marrow treatment. In some embodiments, the bone marrow treatment may comprise about 200 μl of i.v. injections (in the lateral tail vein) containing $5 \times 10^6$ T-cell depleted bone marrow cells. After treatment, IOP measurements of the mice are taken, the optic nerves are analyzed, axons are counted, and the retinas are analyzed. The complete details are set forth in the example below.

It is found that the treated animals may still experience elevated IOP over time, but the treated animals do not experience optic nerve damage and do not develop glaucoma. Further, the method of the present invention prevents the loss of axons of the RGCs, the loss of somas of the RGCs, and the change in morphology of the somas in the animals. The treatment confers protection against neurodegeneration in animal of an age when RGC degeneration is usually very severe and essentially complete in the majority of untreated mice. The finding that optic nerve damage and the physical symptoms of glaucoma may be reduced without reducing IOP is unexpected.

In yet another aspect, the invention provides for a method of selecting and screening candidate substance and/or treatments for degenerative diseases, particularly degenerative diseases of the eye, such as those that accompany the onset and progression of glaucoma. In some embodiments, the method comprises the use of a model for selecting glaucoma-associated neurodegenerative inhibiting agents in an animal, this model being a DBA/2J mouse.

In some embodiments, the method comprises administering to an area of interest of a test animal having glaucoma-associated neurodegeneration an amount of a test agent, and measuring the amount of glaucoma-associated neurodegeneration in said animal to provide a potential neuroprotective activity test value; administering to an area of interest of a control animal having glaucoma-associated neurodegeneration an effective amount of radiation and measuring the amount of glaucoma-associated neurodegeneration in said animal to provide a control neuroprotective baseline value for a glaucoma-associated neuroprotective agent; comparing the test value to the control neuroprotective baseline value; and selecting a test agent or treatment regimen that demonstrates a test value of 50% or more of the control neuroprotective baseline value as a potential agent for inhibiting glaucoma-associated neurodegeneration. In some embodiments, treatment regimes or agents that provide 60%, 70%, 90% or essentially 100% of the neurodegenerative protective effect of the control neuroprotective baseline value may be selected as a candidate substance for the treatment of glaucoma-associated neurodegeneration.

In some embodiments, the method involves protectively inhibiting glaucoma of an eye of a subject at the risk of developing a form of glaucoma (including hereditary forms) comprising administering a treatment regimen comprising administering x-ray radiation in a neurodegeneration-inhibiting amount to a head or eye area of a subject, to thereby protectively inhibit the eye of the subject against neurodegeneration caused by the form of glaucoma. In some embodiments, the method involves protectively inhibiting glaucoma of an eye of a subject having or predisposed to a hereditary form of glaucoma, comprising the following steps: administering x-ray radiation in a neurodegeneration-inhibiting amount to a head or eye area of a subject, to thereby protectively inhibit the eye of the subject against neurodegeneration caused by the hereditary form of glaucoma; and administering to the subject a volume of bone marrow cells.

BRIEF DESCRIPTION OF THE DRAWINGS

The invention will be described in conjunction with the accompanying drawings, in which:

FIGS. 1A through 1F, are images of the iris of diseased mice at different time intervals showing the effect on the iris of treated and untreated mice;

DETAILED DESCRIPTION

Figure 1G:
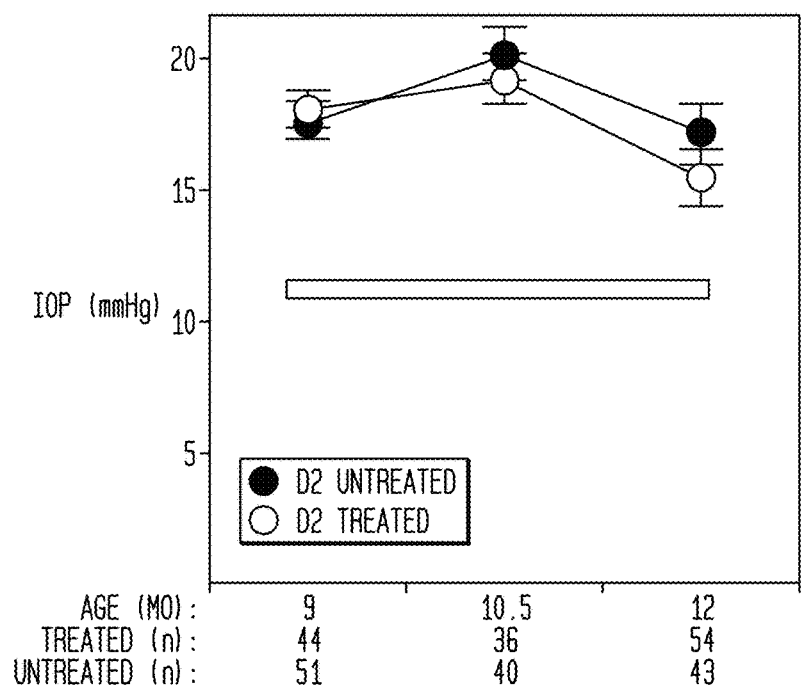
FIG. 1G is a graph, showing clinical disease progression and glaucomatous insult is not influenced by radiation treatment.

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For purposes of the present invention, it should be noted that the singular forms, "a", "an", and "the" include reference to the plural unless the context as herein presented clearly indicates otherwise.

For purposes of the present invention, the term "glaucoma" refers to a group of neurodegenerative diseases characterized by a specific pattern of retinal ganglion cell death and optic nerve atrophy, often associated with elevated intraocular pressure (IOP). The term glaucoma includes, but is not limited to: primary open angle glaucoma, normal pressure glaucoma, primary juvenile glaucoma, acute angle closure glaucoma, intermittent angle closure glaucoma, chronic angle closure glaucoma, primary congenital glaucoma, primary infantile glaucoma, and/or glaucoma associated with congenital anomalies.

For purposes of the present invention, the term "age-related form of glaucoma" refers to forms of glaucoma associated with aging (including hereditary forms), in that the symptoms of glaucoma become manifest in the later years of the subject, for example, after about 40 or more years in the case of humans, or after about 5 or more months in the case of DBA/2J mice.

For purposes of the present invention, the term "neurodegeneration" refers to the damage, loss and/or death of nerve cells.

For purposes of the present invention, the term "neuroprotective" refers to guarding or protecting against a destructive or poisonous effect upon nerve tissue.

For purposes of the present invention, the term "neurodegeneration-inhibiting amount" is an amount or dose regimen of radiation, specifically gamma irradiation and x-ray radiation, that is sufficient to elicit a reduction or inhibition of the amount, extent, severity or incidence of a detectable neurodegenerative physiological event in an animal, compared to the amount, extent, severity or incidence of a detectable neurodegenerative physiological event in an animal not having been treated with the same or similar amount or dose regimen of radiation. By way of example, such an amount to be administered to a targeted area of the body, such as the head or the eye region, would be in the range of about 1 to about 15 Gy, preferably in the range of about 5 to about 10 Gy, or given in fractions by repeated treatment in the range of about 1.0 Gy to about 5.0 Gy, preferably about 2.5 Gy.

For purposes of the present invention, the term "x-ray radiation" refers to electromagnetic ionizing radiation having a wavelength in the range from about 0.01 to about 10 nanometers, and energies in the range of from about 120 eV to about 120 keV. In the human eye, x-ray radiation has a penetration depth of between 0 mm to at least 30 mm, depending on the energy utilized and the time of exposure provided. For the purpose of the present invention the penetration depth of x-ray radiation is controlled to allow for interaction of the x-rays with the posterior portion of the eye.

For purposes of the present invention, the term "gamma radiation" refers to electromagnetic ionizing radiation having frequencies above $10^{19}$ Hz and therefore energies above 100 keV and wavelength less than 10 picometers, often smaller than an atom. Gamma radioactive decay photons commonly have energies of a few hundred KeV, and are almost always less than 10 MeV in energy. In the human eye, gamma radiation fully penetrates all soft tissues. For the purpose of the present invention the penetration depth of gamma radiation allows for interaction of gamma rays with at least the posterior portion of the eye and possibly extended portions of the optical nerve.

For purposes of the present invention, the term "whole body radiation" refers to treatment regimes that deliver whole body radiation in the range of about 8 Gy to about 14 Gy up to a maximum of about 15 Gy, given in fractions in the range of about 1.0 Gy to about 5.0 Gy, preferably about 2.5 Gy.

For purposes of the present invention, the term "radiation dose" as it is used when the radiation treatment is administered as part of a single dose regimen to a defined area of the body, such as the head area, or more particularly to the eye area, is a dose of radiation comprising a range of about 1 Gy to about 40 Gy, or in a range of about 5 Gy to about 10 Gy. In other, embodiments, the term "radiation dose", as it is used when radiation treatment is administered in two approximately equal doses, the dose of radiation comprises an initial and/or first dose of radiation in a range of about 5 Gy to about 7 Gy, and a subsequent and/or second dose or doses of radiation in a range of about 5 Gy to about 7 Gy, or preferably two or more approximately equal doses of about 5 Gy. In other embodiments, the term "radiation dose", as it is used when radiation treatment is administered in a multiple treatment regimen, is defined as a radiation dose comprising about 1.0 Gy to about 5.0 Gy, or preferably about 2.5 Gy and may be any combination of doses so long as the treatment regimen does not exceed 40 Gy. For purposes of the present invention, the term "rads" refers to a unit of absorbed dose of ionizing radiation equal to energy of 100 ergs per gram of irradiated material.

For purposes of the present invention, the term "Gray" or "Gy" refers to the international system unit of radiation dose expressed in terms of absorbed energy per unit mass of tissue. The gray is the unit of absorbed dose and 1 gray=1 Joule/kilogram and also equals 100 rad. In embodiments involving administration of, for example, x-ray radiation, the radiation dose may be in the range of from about 1 Gy to about 15 Gy, for example, from about 5 Gy to about 10 Gy, such a from about 5 Gy to about 7 Gy.

For purposes of the present invention, the term "cGy" refers to centigray. 1 cGy=1 rad.

For purposes of the present invention, the term "protectively inhibiting" refers to a treatment which may prophylatically contribute to inhibiting, minimizing, reducing, preventing, etc., an underlying cause of a neurodegenerative disease.

For purposes of the present invention, the term "protectively inhibiting glaucoma" refers to a treatment which may prophylatically contribute to inhibiting, minimizing, reducing, preventing, etc., an underlying cause of the glaucoma (e.g., neurodegeneration).

For purposes of the present invention, the term "area of the body" refers to a portion or area of the body that does not include the entire body. By way of example, an area of the body is the head area, the eye area, or the face area, or any portion of these areas that include the eye or eyes of an animal.

For purposes of the present invention, the term "syngeneic" refers to genetically identical or similar especially with respect to antigens or immunological reactions.

For purposes of the present invention, the term "autologous" refers to something that is derived from the same individual.

For purposes of the present invention, the term "hematopoietic" refers to forming blood or blood cells.

For purposes of the present invention, the term "heterologous" refers to something that is derived from a different species, as a graft or transplant.

For purposes of the present invention, the term "midplane" refers the mid point of the mouse body with the plane orientated at right angles to its spine to the pelvic plane of least dimensions.

For purposes of the present invention, the term "DBA/2J mice" refers to a naturally occurring mouse model of glaucoma, wherein the mice develop an age-related form of hereditary glaucoma initiated by mutations in two genes, Tyrp1 and Gpnmb.

For the purpose of this invention, the term "indication of glaucoma" means: an increase in IOP which if left unchecked will result in ocular damage, and/or an abnormal disc ratio.

For the purpose of this invention, the term "onset of glaucoma or glaucoma manifestations" means ocular damage as a result or manifested by: an increase in IOP, visual field decline, and/or an abnormal disc ratio where ocular damage is present.

DESCRIPTION

The embodiments of method of the present invention provide a very reproducible and long-lasting neuroprotective treatment. Potential, non-mutually exclusive mechanisms for conferring the neuroprotective treatment of the present invention include neuronal preconditioning, altered immune responses, radiation-sensitive cell types, trophic factors, glial changes, and stem/precursor cells.

Figure 8:
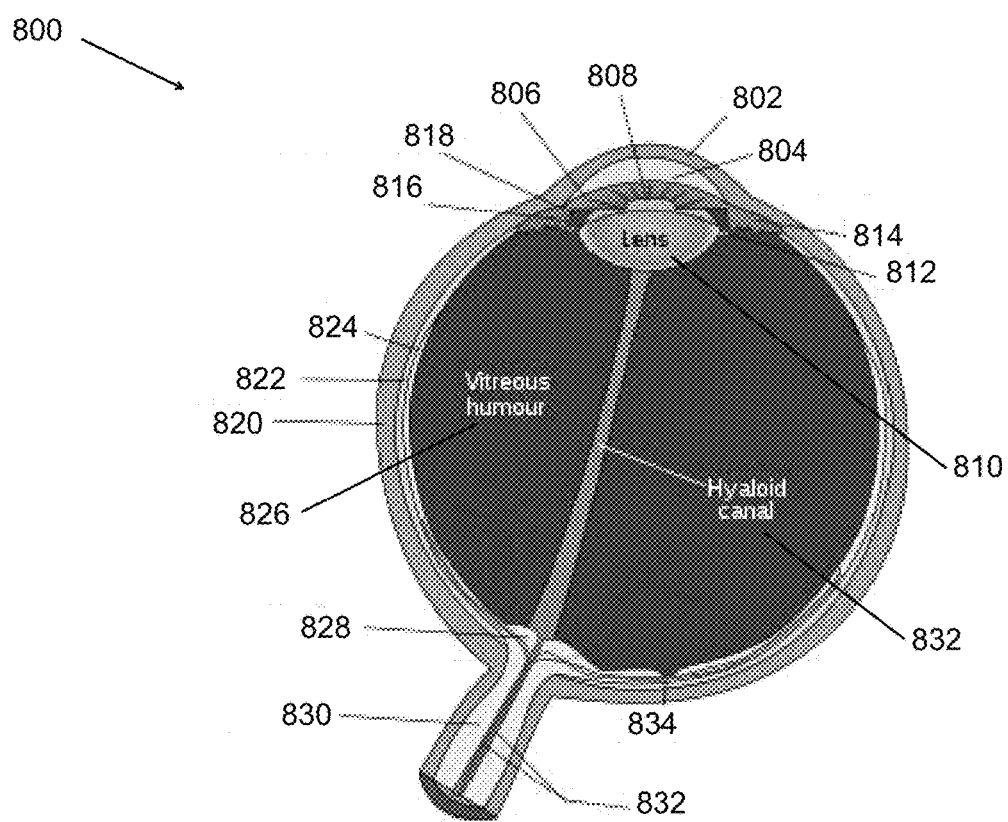
FIG. 8 is a cross section of a human eye.

In order to fully understand the teachings of the present invention, one must first understand the physical structure of the eye. Turning now to FIG. 8, a human eye 800 is illustrated. As may be seen, eye 800 comprises a cornea 802 which is disposed above an anterior chamber 804. Disposed below anterior chamber 804 is an iris 806 which covers pupil 808. Lens 810 is disposed below pupil 808 and is maintained in position by suspensory ligaments 812 and ciliary muscles 814. Zonular fibers 816 connect ciliary muscles 814 to ligaments 812. A posterior chamber 818 is defined by the borders of iris 806, muscle 814 and ligament 812. Eye 800 is encased in a sclera 820. A vascular layer of connective tissue, known as the choroid 822, is disposed between sclera 820 and retina 824. Retina 824 is a light sensitive tissue lining the inner surface of eye 800. As may be see, retina 824 is located in the posterior section of eye 800. A clear gel, known as the vitreous body 826, fills the space between retina 824 and lens 810. An optic disc or optic nerve head 828 connects retina 826 to optic nerve 830. Hyaloid canal 832 extends from optic disc 828 through vitreous humor 826 to lens 810. Blood is provided to eye 800 by retinal blood vessels 832 Finally, the fovea 834 is disposed in retina 824.

In a typical human, eye 800 may be approximated by a spherical shape having a diameter in the range 23-29 mm. It should be understood that only a very small portion of eye 800 physically exposed to allow for treatment to be administered to the eye. In fact, one critical aspect of the teachings of the present invention is the use of methods for reaching the posterior section of the eye. For the purpose of the present application, the posterior portion of the eye is defined as retina 824, optic disc 828 optic nerve 830, the blood vessels located therein, and the myelin junction region of the optic nerve.

In order to fully understand the teachings of the present invention, one must first understand the traditional diagnostic and treatment protocols used in the treatment of nerodegerative disease such as glaucoma. Traditionally, this has involved first detecting the disease and then treating the disease when it is in an advanced state.

The development of neurodegeneration in a patient may be divided into the following phases: 1) At risk or pre-glaucoma, 2) asymptomatic damage, 3) early glaucoma or moderate glaucoma, 4) symptomatic damage and advanced glaucoma, and 5) far advanced glaucoma. We will now discuss these phases of the disease with reference to the existing protocols for detection and treatment.

During the first phase, at risk or pre-glaucoma, the primary technique utilized for assessing risk is family history. Recently, there have been significant developments in genetic testing for glaucoma. Additionally, the use of disc variation as a factor for detecting glaucoma may be utilized. In particular, research has shown that the disc ratio correlates positively with subsequent visual field decline. It has been found that the cup to disk ratio of 0.1 is average. If this ration exceeds 0.5, there is a strong correlation to the development of glaucoma. This test would be helpful if consistently conducted at the clinical level. Unfortunately, this test is not consistently utilized at this stage.

Intraocular pressure (IOP) is the best known risk factor that may be modified and detected on clinical exam, A high or elevated IOP (>21 mmHg) is a risk factor for glaucoma. IOPs in 20 mmHg values are often present before glaucoma manifestation. This test would be helpful if consistently conducted at the clinical level. Unfortunately, this test is not consistently utilized at this stage, depending on the age of the patient.

In particular, genes associated with glaucoma include, but are not limited to: GLC1A (1q24), GLC1B (2-cen-q13), GLC1C (3q21-q24), GLC1D (8q23), GLC1E (10p14-p15), GLC1F (7q35-q36), GLC3A (2p21 Cytochrome), P4501B1 (CYP1B1), and GLC3B (1p36.2-36.1). These genetic markers may be utilized in generic screens for determining the likelihood of developing glaucoma before the onset of the disease. Currently, there are no genetic tests being utilized in the at risk or pre-glaucoma phase.

It should be appreciated that there is no existing treatment protocol for the at risk or pre-glaucoma stage. There is a very long pre-symptomatic phase of the disease during which early identification and treatment would benefit the sufferer. None of the above tests address this pre-symptomatic phase and no existing treatments are provided during this pre-symptomatic phase due to cost, potential side effects, and many will never develop glaucoma. Thus, deterioration occurs before treatment is initiated.

The only clinical approach utilized in the at risk or pre-glaucoma stage is to monitor for deterioration. Thus, there is a need for the prophylactic treatment of neurodegeneration at this stage. One aspect of the present invention is to provide for a treatment regimen comprising administering radiation in a neurodegeneration-inhibiting amount to a head or eye area of a subject having a potential for developing glaucoma, to thereby protectively inhibit the eye of the subject against neurodegeneration caused by glaucoma, prior to the onset of any indication of glaucoma. This novel approach allows for the retardation and possibly for the prevention of glaucoma from manifesting later stages in the patient. The treatment regimen has not been utilized or even contemplated in the prior art treatment regimen.

During the second phase, asymptomatic damage, the primary technique utilized for diagnosis is the serial study of the optic disk (disk ratios), nerve fiber layer, and angle.

Once again, it should be appreciated that there is no existing treatment protocol for the asymptomatic damage stage. Even worse, damage is now physically manifest but has not presented any traditional symptoms associated with glaucoma. Unfortunately, since the damage has not noticeably affected visual field acuity, the patient is unlikely to seek medical attention.

The only clinical approach utilized in the at risk or pre-glaucoma stage is to monitor for deterioration for those patients that have requested medical attention. Thus, there is a need for the prophylactic treatment of neurodegeneration at this stage. One aspect of the present invention is to provide for a treatment regimen comprising administering a treatment regimen comprising administering radiation in a neurodegeneration-inhibiting amount to a head or eye area of a subject being a suspect of developing glaucoma manifestations, to thereby protectively inhibit the eye of the subject against neurodegeneration caused by glaucoma, prior to the onset of glaucoma manifestations.

During the third phase, early glaucoma or moderate glaucoma (i.e. where damage has occurred), the primary technique utilized for diagnosis is the serial study of the optic disc and visual field. At the clinical level, the manifestation of the presence or absence of visual field decline is utilized as a test to determine the onset of early glaucoma or moderate glaucoma. The primary drawback to this approach for detection is that damage has already occurred and the disease has manifested itself. Thus, this screen is a confirmatory screen for the existence of the disease. The only clinical approach utilized in the at risk or pre-glaucoma stage is to monitor for deterioration. Thus, there is a need for the treatment of neurodegeneration at this stage. One aspect of the present invention is to provide for a treatment regimen comprising administering a treatment regimen comprising administering radiation in a neurodegeneration-inhibiting amount to the eye of a subject having glaucoma, to thereby further inhibit the eye of the subject against neurodegeneration caused by glaucoma, wherein radiation in a neurodegeneration-inhibiting amount interacts with posterior portions of the eye.

During the fourth and fifth phase, symptomatic damage and advanced glaucoma, and 5) far advanced glaucoma, the primary technique utilized for diagnosis is the use of intraocular pressure (IOP). There have been numerous studies which provide a correlation between elevated IOP and the onset of early to moderate glaucoma. Generally, when IOP is greater than 16 to 21 mm Hg, it may be an indicator of symptomatic damage and advanced glaucoma. When IOP is over 25 there is a very strong correlation to the development of far advanced glaucoma. This simplistic model has several disadvantages. First, an individual's, optic nerve has a level of IOP that it either can or cannot withstand. Thus, the range for IOP to be an indicator is highly variable by individual. In fact, many if not the majority of individuals with an elevated IOP never develop glaucoma, while other individuals develop glaucoma with IOPs at the normal population average of 16 mmHg. Second, by the time that high IOP is detected, significant damage may have already begun and the disease has already occurred. It should be appreciated the in many patients IOP is most likely high before damage occurs. The issue is high IOP is not typically symptomatic and so the patient does not know about it unless screened. Thus, IOP is often first detected when glaucoma is advanced. Some individuals do not have an eye exam until they already have a visual problem and so elevated IOP is detected when disease is advanced or already manifested. Thus, the use of IOP may be used as a risk factor but is not determinative of the onset of the disease. Other factors that have been utilized are the presence of myopia, family history, diabetes and systemic hypertension.

During the fourth phase, treatments usually involve the reduction of IOP via non-invasive mechanisms. Generally, this stage of treatment involves hypertensive drops or medications to treat elevated IOP. Classes of IOP agents include, but are not limited to: cholinergic agents such as parasympathomimetics and miotics; aderenergic agents such as epinephrine compounds; agonists; beta blockers; oral and topical carbonic anhydrase inhibitors; and prostaglandin analogues. It should be appreciated that all of these techniques focus on the treatment of IOP and do not directly treat the existing glaucoma. Thus, these treatments have varying success, depending on the patients particular IOP sensitivity.

Thus, there is a need for the treatment of neurodegeneration at this stage. One aspect of the present invention is to provide for a treatment regimen comprising administering radiation in a neurodegeneration-inhibiting amount to an optic nerve head of a subject having glaucoma, to thereby further inhibit the eye of the subject against neurodegeneration caused by glaucoma, wherein radiation in a neurodegeneration-inhibiting amount interacts with the optic nerve head.

In another embodiment of the invention, a treatment regimen is provided and comprises administering radiation in a neurodegeneration-inhibiting amount to an optic nerve as it exits the eye of a subject having glaucoma, to thereby further inhibit the eye of the subject against neurodegeneration caused by glaucoma, wherein radiation in a neurodegeneration-inhibiting amount interacts with the optic nerve as it exits the eye.

In another embodiment of the invention, a treatment regimen is provided and comprises administering radiation in a neurodegeneration-inhibiting amount to a retina of a subject having glaucoma, to thereby further inhibit the eye of the subject against neurodegeneration caused by glaucoma, wherein radiation in a neurodegeneration-inhibiting amount interacts with the retina.

In another embodiment of the invention, a treatment regimen is provided and comprises administering radiation in a neurodegeneration-inhibiting amount to myelin junctions of a subject having glaucoma, to thereby further inhibit the eye of the subject against neurodegeneration caused by glaucoma, wherein radiation in a neurodegeneration-inhibiting amount interacts with the myelin junctions.

During the fifth phase, treatments usually involve the reduction of IOP via invasive mechanisms. These mechanisms include the use of laser treatment and traditional surgery. Once again, all of these techniques focus on the treatment of IOP and do not directly treat the existing glaucoma. In addition, these techniques also have the added disadvantage of being highly invasive techniques with modify the eye structure by having an incision therein or thereon. These treatments have varying success, depending on the patients particular IOP sensitivity.

As a follow-up to either laser or traditional surgery, the patient may be treated with beta radiation to reduce scarring. Of the three common types of radiation given off by radioactive materials, alpha, beta and gamma, beta radiation has the medium penetrating power and the medium ionizing power. Although the beta particles given off by different radioactive materials vary in energy, most beta particles can be stopped by a few millimeters of aluminum or other material. Being composed of charged particles, beta radiation is more strongly ionizing than gamma radiation. When passing through matter, a beta particle is decelerated by electromagnetic interactions and thus has a very low penetration depth. For example, beta radiation generated from a Sr source loses 50% of its energy after penetrating 1.5 mm of water, and the $^{106}$Ru source loses 50% of its energy after penetrating 2.4 mm.

In the human eye, beta radiation has a penetration depth of between 0.0 mm and 4.6 mm for the doses utilized with the present invention. As stated above, beta radiation has a very limited depth penetration in the eye. Thus, its use is limited to the reduction of scarring at or near the surface of the eye. Because of this limited penetration, there is no interaction between the beta radiation and the posterior portion of the eye.

There is a need for the treatment of neurodegeneration at this stage. One aspect of the present invention is to provide for a treatment regimen comprising administering radiation in a neurodegeneration-inhibiting amount to a head or eye area of a subject having glaucoma, to thereby further inhibit the eye of the subject against neurodegeneration caused by glaucoma, wherein radiation is delivered to the subject prior to an incision to the eye.

Turning now to the teachings of the present invention, it has been found that the use of properly applied radiation may significantly effect neurodegeneration in mammals. We will now turn to the specific teachings of the present invention as discussed above.

Figure 6:
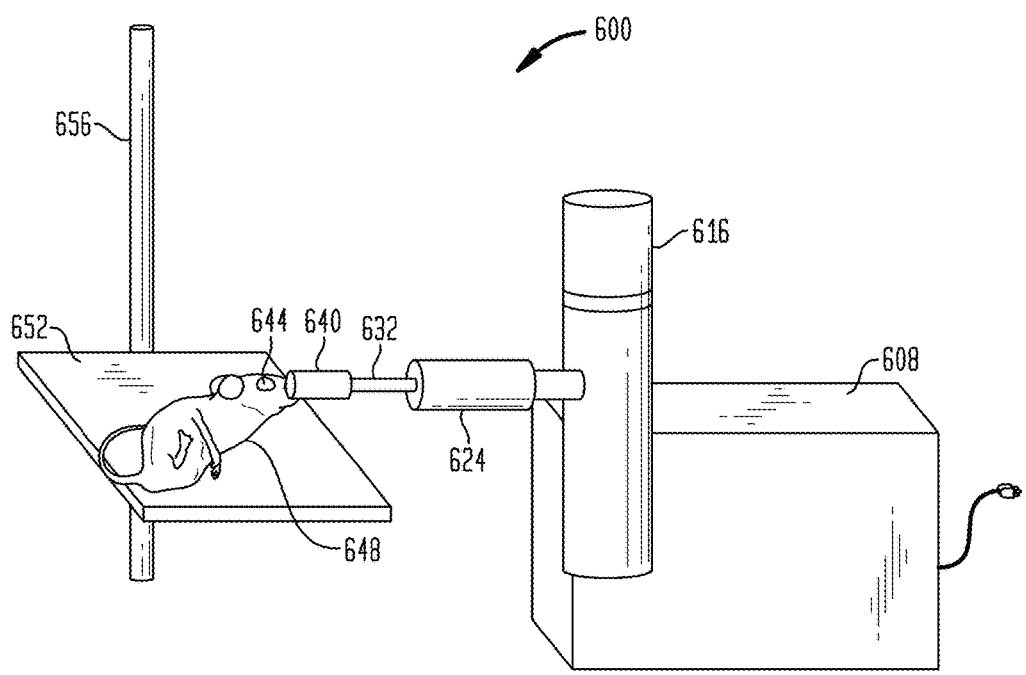
FIG. 6 is a perspective view of a system for administering x-ray radiation to the eye of a subject.

A system for providing x-ray radiation treatment to the eye region is illustrated in FIG. 6, and is referred to generally as 600. System 600 includes a machine for delivering a focused radiation beam (AXT, Inc.) indicated generally as 608. In an embodiment, the radiation beam is x-rays and in another embodiment the radiation beam is gamma radiation. Machine 608 has a radiation tube, indicated as 616, for generating radiation of desired type, strength, and power to provide a neurodegeneration-inhibiting amount of the radiation. Radiation generated by tube 616 is delivered to and a focused by a collimator, indicated generally as 624, to more narrowly focus the radiation to provide a delivery area having diameter appropriate for administration to the eye of the subject. For example, collimator 616 may focus the radiation to provide a delivery area having a diameter of at least about 10 microns, such as at least about 50 microns. Focused radiation from collimator 624 is transmitted through an optical channel, e.g., fiber optic cable, indicated generally as 632, to a radiation delivery lens, indicated generally as 640.

As shown in FIG. 6, radiation is transmitted by lens 640 to the eye 644 of the subject, for example, mammal 648. Mammal 648 is restrained by means (not shown) so that a therapeutic dose of x-ray radiation may be delivered to eye 644 by lens 640. Mammal 648 is shown in FIG. 6 as resting (while being restrained) on a generally horizontally extending platform 652. Platform 652 is supported and elevated by a stand, indicated generally as 656. It should be appreciated that platform 652 would be modified to address the specific needs of the patient being treated.

It should be appreciated that other mechanisms may be utilized to deliver radiation treatment to the eye. For example, a system is disclosed in U.S. Patent Application 2009/0022274 which discloses a system for aiming radiation for treatment purposes. The entire disclosure and contents of this application is incorporated herein by reference in its entirety.

Turning now to FIG. 1A through 1F, FIGS. 1A-1F, are images, while FIG. 1G is a graph, showing clinical disease progression and glaucomatous insult is not influenced by radiation treatment. The overall clinical presentation of the iris disease is indistinguishable between treated and untreated groups. Typical images of mice of the indicated ages and treatment groups are shown. The only clinical difference in ocular phenotypes between untreated and treated cohorts was that all treated mice developed radiation induced lens opacities. At 9 months, characteristic peripupillary swellings and dispersed pigment accumulations are evident in both treated and untreated mice. At this age, the degree of peripupillary iris atrophy (evident as white tissue adjacent to the pupil) varies from eye to eye in each treatment group (see FIGS. 1C and 1D). At 12 months, dispersed pigment is clearly evident on the lens and across the surface of the iris (see FIGS. 1E and 1F). At 14 months, there is advanced iris atrophy, which is not restricted to the peripupillary area. Full-thickness iris holes and severely atrophic areas that appear thin and depigmented occur in both groups (see FIG. 1G). IOP profiles showing that treatment did not change the glaucomatous IOP insult (mean±SEM). The thickness of the gray line represents the mean IOP±SEM (11.3±0.25, n=31) for DBA/2J mice at an age before ocular disease (3 months). The number of successful IOP recordings at each age are indicated.

Figure 2C:
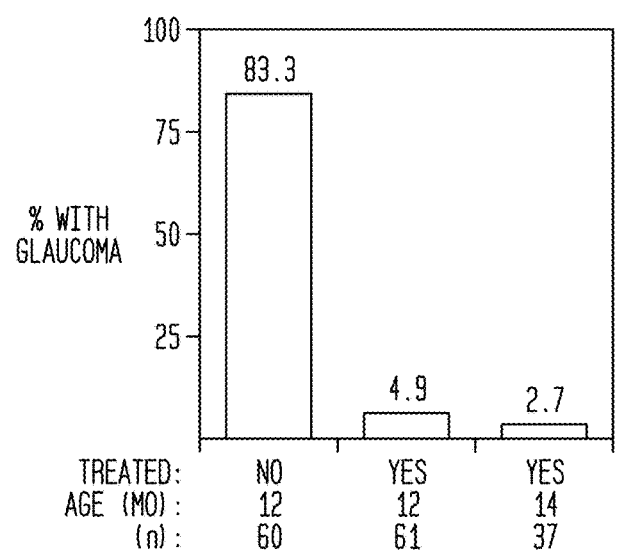
FIG. 2C is a bar graph, showing treated mice are protected from glaucomatous neurodegeneration with the use of the teachings of the present invention.
Figure 2A:
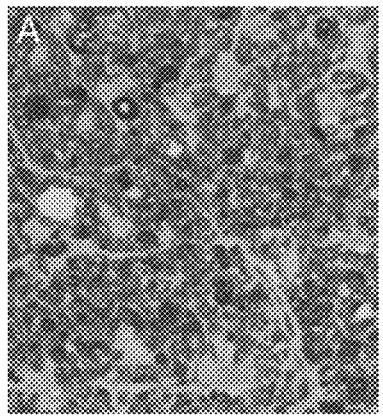
FIGS. 2A, 2B, are images of optic nerves and 2D through 2F, are retinal images, where the optic nerves are stained with paraphenylenediamine to visualize the myelin sheath of all axons, and differentially darkly stain the axoplasm of damaged and dying axons and the retinas are stained to visualize retinal ganglion cells.
Figure 2B:
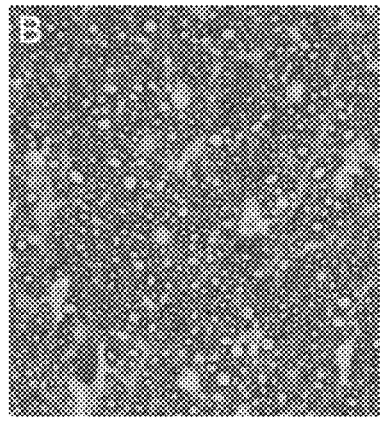
Figure 2D:
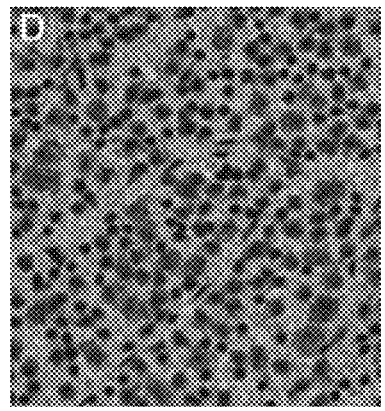
Figure 2E:
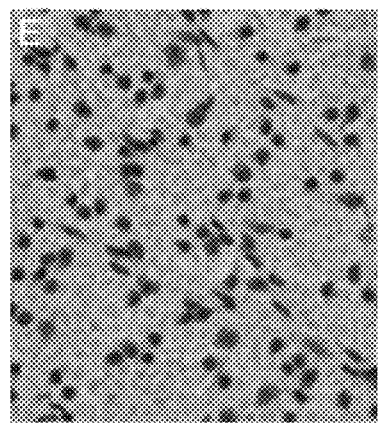
Figure 2F:
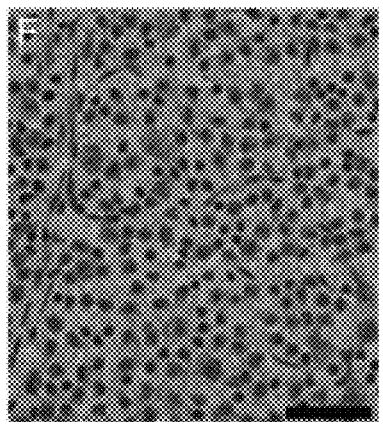

Turning now to FIG. 2A through 2F, FIGS. 2A-2B and 2D-2F, are images, while FIG. 2C is a bar graph, showing treated mice are protected from glaucomatous neurodegeneration. Optic nerves are stained with paraphenylenediamine to visualize the myelin sheath of all axons, and differentially darkly stain the axoplasm of damaged and dying axons. This is an extremely sensitive technique that allows for the detection of a single sick/dying axon in the optic nerve which are almost completely composed of normal healthy axons (see FIG. 2B). By 12 months, the majority of optic nerves from untreated DBA/2J mice have severe glaucoma, as defined by massive axon loss (see FIG. 2A). The vast majority of optic nerves from treated mice had no detectable glaucomatous damage, even out to 14 months (see FIG. 2C). A summary of the data from 12- and 14-month-old mice clearly demonstrates the protective effect of treatment, which prevents glaucomatous neurodegeneration in the vast majority of eyes. Because the results did not differ, the data from the experiments at independent times are combined (see FIG. 2C). Nissl-stained flat-mounted retinas from position-matched regions of the superior peripheral retina also demonstrate the profound protective effect of treatment (n=5 flat mounted retinas per group). Young DBA/2J mouse showing normal density of ganglion cell layer cells before glaucomatous damage (see FIG. 2D). Twelve-month-old untreated DBA/2J mouse, showing substantial reduction in the number of soma as a result of glaucoma (see FIG. 2E). Twelve-month-treated DBA/2J mouse with normal number of soma (Scale bar, 50 μM) (see FIG. 2F).

Figure 3A:
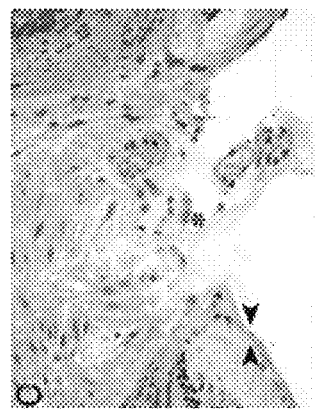
FIGS. 3A-3F are images showing that utilizing the teachings of the present invention prevents glaucomatous optic nerve excavation.
Figure 3B:
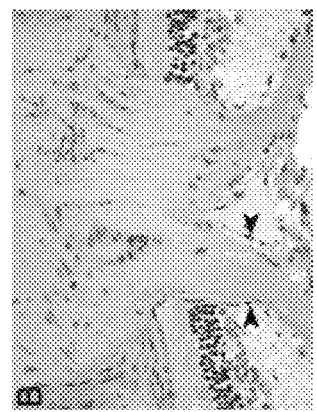
Figure 3C:
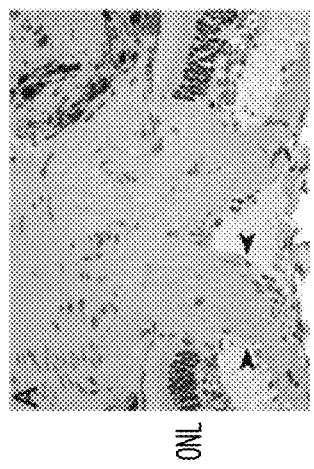
Figure 3D:
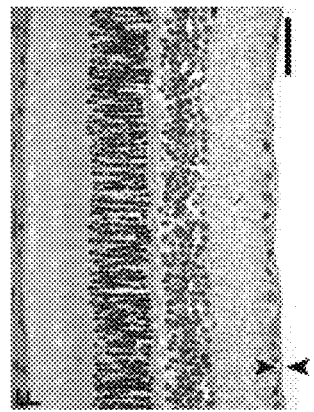
Figure 3E:
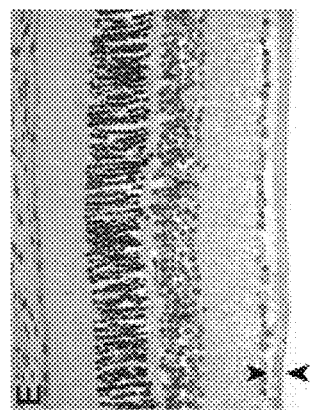
Figure 3F:
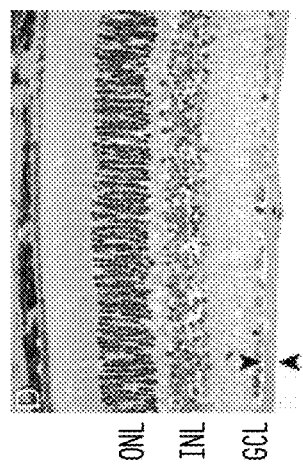

FIGS. 3A-3F are images showing treatment prevents glaucomatous optic nerve excavation (see FIG. 3B). The optic nerve heads of control nonglaucomatous DBA/2J mice include large numbers of axons, as evidenced by a thick nerve fiber layer, entering the optic nerve head (nerve fiber layer on left side of optic nerve head is marked by arrowheads) (see FIG. 3A). The thickness of the nerve fiber layer in treated DBA/2J mice (14-month-old example) is indistinguishable from nonglaucomatous controls (see FIG. 3B). In contrast, untreated DBA/2J mice have severe axon loss, as evidenced by a very atrophied nerve fiber layer (see FIG. 3C). Their optic nerve heads are also severely excavated (asterisk), a hallmark of glaucoma (12-month example). See FIG. 3D-3F showing position-matched images of retinal cross sections) with FIG. 3D showing nonglaucomatous DBA/2J control mouse, FIG. 3E showing treated DBA/2J mouse, 14 months old, and FIG. 3F showing untreated DBA/2J mouse, 12 months old. The nerve fiber layer (arrowheads) is of normal thickness in treated DBA/2J retina (compare FIG. 3D with FIG. 3E) and severely atrophied in the untreated glaucomatous DBA/2J retina (compare FIG. 3D with FIG. 3F). There is an obvious loss of somas in the ganglion cell layer (GCL) of the untreated DBA/2J mouse (see FIG. 3F) but not in the treated DBA/2J mouse (see FIG. 3E; compare both to control retina in FIG. 3D). ONL, outer nuclear layer; INL, inner nuclear layer. (Scale bar, 50 μm.)

Figure 4:
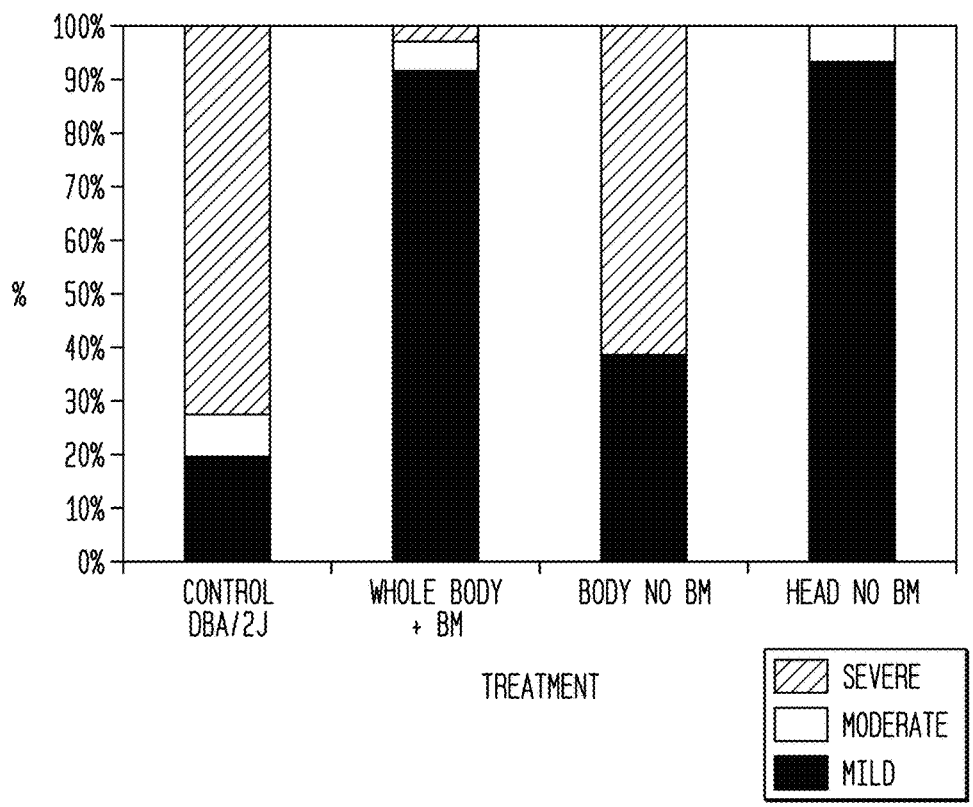
FIG. 4 is a bar graph showing the effect of part body irradiation on glaucomatous optic nerve damage.

FIG. 4 is a bar graph showing the effect of part body irradiation on glaucomatous optic nerve damage. Treatment groups: Control/DBA/2J; Whole Body+Bone Marrow; Body/No Bone Marrow; Head/No Bone Marrow. (/// (cross hatched)=Severe Damage; ☐ (open bar)=Moderate Damage; ■ (solid bar)=Mild Damage).

Figure 5:
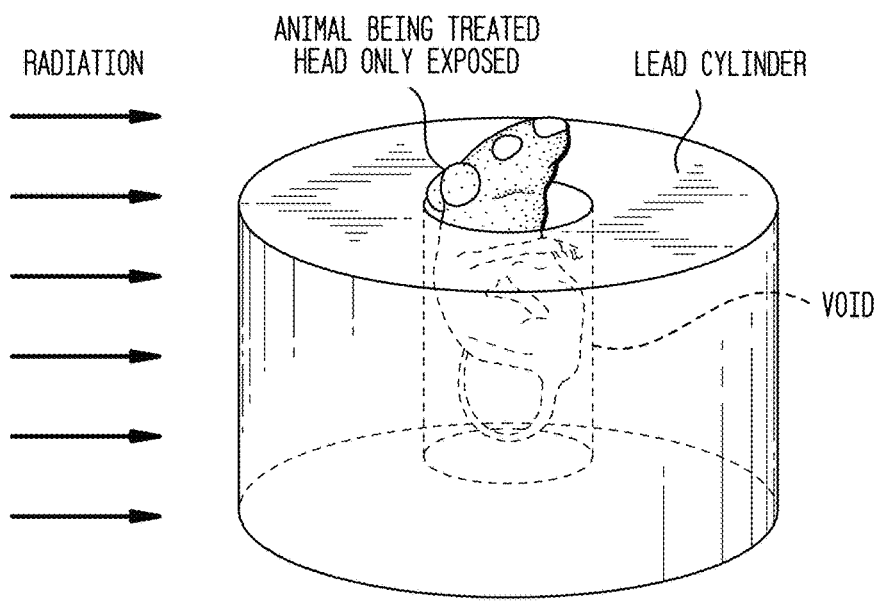
FIG. 5 shows an apparatus constructed in accordance with an embodiment of the invention.

FIG. 5 shows an apparatus where anesthetized mice were placed in the void in the lead cylinder with packing to prevent a change in orientation within the cylinder, only the head region is exposed to radiation. The cylinder is placed upright in the irradiator (following the procedure set forth in Anderson et al. (2005), PNAS, 102(12):4566-4571). Mice were irradiated with 1000 rads, the cylinder was placed on a slowly rotating platform to ensure even radiation. Radiation was applied from a 137Cs source in two equal doses of 500 rads spaced 3-4 hours apart.

EXAMPLES

The following non-limiting examples are illustrative of the present invention, and should not be construed to constitute any limitation of the invention as it is described in the claims appended hereto.

Example 1—Whole-Body Radiation and Bone Marrow Method

The present example is provided to demonstrate the utility of the present invention in an animal model accepted by those of skill in the art as predictive of human forms of glaucoma. By way of example, the form of glaucoma is an age-related form of hereditary glaucoma initiated in DBA/2J mice by the mutation of two genes, Tyrp1 and Gpnmb, see John et al. (1988)[36]; Chang et al. (1999)[37]; and Anderson et al. (2002)[38].

Animal Model for Glaucoma:

The DBA/2J mouse model for glaucoma was used in the present study, and is an accepted model for glaucoma in humans.

DBA/2J mice were fed a 6% fat (NIH31) diet ad libitum, and drinking water was acidified to a pH of 2.8-3.2. Mice were housed in cages containing white pine bedding and kept in a 21° C. environment with a 14-h light and 10-h dark cycle.

Bone Marrow Preparation:

The methods used for harvesting and re-infusion of bone marrow in human subjects are generally modifications of the techniques known in the art (Thomas E D, Storb R., (1970)[32]). Prior to being subjected to high-dose radiation, marrow is preferably harvested by repeated aspirations from the posterior iliac crest until an adequate number of cells have been removed. If a sufficient number of cells cannot be obtained from the posterior iliac crest, marrow can also be harvested from the anterior iliac crest and the sternum. The smallest number of nucleated marrow cells required for long-term repopulation in humans is not precisely known. In practice, the number of cells harvested is usually 100 million to 300 million per kilogram of the recipient's body weight and dependent on the type and intensity of the preparative regimen and whether the marrow graft will be modified in vitro, see Buckner C D, et al. (1984)[33]; Bortin et al. (1983)[34]; Kessinger A, Armitage J O, (1987)[35]. Thus, the effective range of cells harvested may be between about 75 million and about 400 million per kilogram and be considered within the scope of the teachings of the present invention.

Generation of Bone Marrow Chimeras:

Bone marrow chimeras were generated as follows: 5-8-week-old female DBA/2J mice were irradiated with 1,000 rads of whole-body radiation. During treatment, mice were positioned on a slowly rotating platform to ensure uniform application. Radiation was applied from a 137Cs source in two equal doses of 500 rads spaced 3-4 hours apart. The dose was applied at a rate of 132 rads/minute. Shortly after the second radiation dose, mice received 200 µl of i.v. injections (in the lateral tail vein) containing $5 \times 10^6$ T-cell depleted bone marrow cells. Donor mice in all experiments were 1.7-1.9 months old. Donor marrow was depleted of T lymphocytes with 10 µg/ml purified monoclonal antibodies to CD4 (GK1.5, The Jackson Laboratory Flow Cytometry Service) and CD8a (53-6.72, The Jackson Laboratory Flow Cytometry Service). Before injection, free antibodies were removed by centrifugation.

DBA/2J mice develop a pigmentary form of glaucoma that involves iris atrophy and pigment dispersion. A slit lamp was used to determine whether the treatment altered the course of the disease. Eyes were examined with a slit-lamp biomicroscope and photographed through a 40× objective lens. All exams viewed both the left and right eyes. All photographs were taken by using identical camera and light settings. Assessed phenotypes included the degree and pattern of pigment dispersion, the degree and pattern of iris atrophy, the degree and pattern of transillumination, and the depth of the anterior chamber.

Next, the intra-ocular pressure (IOP) was measured. Mice were acclimatized to the procedure room environment for at least 1 week before measurement. To record IOP, mice were anesthetized by using intraperitoneal injection of ketamine (Ketalar, Parke-Davis, Paramus, N.J.) and xylazine (Rompun, Phoenix Pharmaceutical, St. Joseph, Mo.). Because the IOPs of C57BL/6J are very consistent, C57BL/6J mice were interspersed with experimental mice during all studies as a methodologic control to ensure consistent equipment calibration and performance.

Optic nerve cross sections were examined for glaucomatous damage by using a modified paraphenylenediamine (PPD) staining protocol to stain the myelin sheath of all axons, and the axoplasma of damaged axons. PPD stains all myelin sheaths, but differentially stains the axoplasm of sick or dying axons darkly. Optic nerves were fixed in situ in 0.8% paraformaldehyde, 1.2% gluteraldehyde, 0.08% phosphate buffer, pH 7.4 at 4° C. Sections of nerve between the orbit and chiasm were dissected free, processed, embedded in resin, sectioned, and stained with PPD. Each age group investigated contained left and right nerves. Stained sections were compared with identically processed sections from untreated DBA/2J mice at various disease stages.

Counts of normal appearing axons were performed by using established nonbiased counting methods. Before beginning axon counts, the optic nerve was outlined at ×100 magnification and its cross-sectional area was automatically calculated by using a computer program (METAMORPH, VERSION 4.6r9, Universal Imaging, Downingtown, Pa.). Magnification of the same nerve section was increased to ×1,000, and 20×1,000 fields were electronically collected, covering 80-90% of the nerve. The fields were spaced in a regular fashion across the entire nerve, taking care to avoid field overlap and not count the same area twice. The 20 collected images were stacked on the computer screen so that only the final image was visible to the operator. A rectangular box was then drawn near the center of the 20th image. The program (METAMORPH) then "cut" a rectangle centered at the same location in all 20 images. Because the operator could only see the top image, this action removed the possibility of unconscious operator bias and made the selection of axons to be counted random.

Axons were counted manually and marked by using the computer. The program tracked the total area counted and the total axon count for all 20 images. The total counted area was >10% of the total nerve area. The final count was calculated and expressed as number of axons per optic nerve. Axon counting is used to quantify the number of axons in nerves of each damage level. When performing this procedure, more than eight nerves of each level were randomly selected for counting. Additionally, to quantitatively assess the effects of treatment, axon counting was performed on randomly selected nerves from treated mice and compared with the values for young pre-glaucomatous strain matched controls.

Because of the large number of mice, an optic nerve grading system was used to determine the level of glaucomatous damage in the 158 nerves analyzed in this study. The indicated damage levels are readily distinguishable upon inspection of the nerve without counting. Furthermore, axon counts on a randomly selected subset of DBA/2J nerves of each damage level indicate that the levels represent clearly distinct stages of disease. The damage level for each nerve was scored by taking into account several factors: the number of healthy axons remaining (compared with pre-glaucomatous DBA/2J nerves), the number of damaged axons, and the amount of scarring associated with gliosis.

In many mildly damaged nerves, no axon loss/damage is detected. In other nerves, the minor damage exists that is equivalent to that observed in similarly aged mice of various mouse strains that do not develop glaucoma (≤2% of axons appear damaged). Because the mild damage observed in some of these nerves also occurs in old mice of various strains, this mild stage of damage is not considered glaucomatous damage. The average axon count for nerves graded as mild is 5,888±1,441 (average±SEM, n=11). In moderate nerves, significant numbers of sick/degenerating axons are readily detected in many regions of the nerve, but the majority of remaining axons appear healthy. This stage is almost never seen in non-glaucomatous mice, and therefore, this is considered to be glaucomatous damage. The axon count for nerves graded moderate is clearly reduced (31,410±2,199, n=8, P<0.001), compared with the counts for mild DBA/2J nerves.

Nerves are classified as having severe glaucoma when the number of damaged axons closely approaches, or surpasses, the number of healthy axons. In fact, for the DBA/2J-untreated mice with severe glaucoma in this study, 82% of optic nerves were judged to have fewer than 5% healthy axons remaining, and the other 18% of optic nerves were judged to have <50% healthy axons remaining. The average axon count for severely damaged nerves is 5,454±1,441 (n=24, P<0.001), compared with mild and moderate axon counts.

All nerves were scored by at least two "masked" investigators. Both investigators were unaware of the age of the mouse, or whether the nerve was from a treated or untreated animal. Furthermore, both investigators were unaware of the damage level assigned by the other investigator. Of the 158 nerves analyzed in this study, the investigators assigned the same damage level to approximately 96% of the nerves. In the five cases where the two investigator's grades did not agree, a third investigator (also masked) analyzed the nerve. The third investigator's damage level always agreed with that of one of the first investigators. The most commonly assigned damage level was used as the grade.

For retinal sections, whole eyes were removed and immersion-fixed in 0.8% paraformaldehyde, 1.2% gluteraldehyde, 0.08% phosphate buffer, pH 7.4, overnight at 4° C. Eyes were embedded in resin, sectioned, and stained with hematoxylin/eosin. Flat mounting was performed similarly. Briefly, eyes were marked for orientation, enucleated, and whole eyes were immersion-fixed in 4% paraformaldehyde in 0.1% phosphate buffer overnight at 4° C. Eyes were either processed immediately or stored in 0.4% paraformaldehyde in 0.1% phosphate buffer. Eyes were rinsed in PBS (pH 7.4) and the anterior chamber was removed. The resultant eye cup was incubated overnight in 0.3% Triton X-100 in PBS at 37° C. The neuronal retina was dissected free from RPE and sclera. The free-floating retina was rinsed in PBS and then incubated overnight in 3% $H_2O_2$, 1% $Na_2HPO_4$ at room temperature. Retinas were rinsed in PBS and placed (RGC-side up) onto a microscope slide. After air drying for 5-15 min (until translucent), retinas were flattened overnight under a coverslip with a 10-g weight placed on top. Retinas were then stained by using a brush for approximately 1 min with 1% cresyl violet in water containing 2.5% (freshly added) acetic acid. Stained retinas were dehydrated, washed in xylene, and coverslipped.

The clinical phenotypes and IOP profiles of the treated DBA/2J mice were carefully examined at multiple ages and compared with similarly housed, age-matched, untreated mice. IOP was monitored at three key ages during the period of glaucoma-inducing IOP elevation in this mouse strain. No differences were detected between the treated and untreated groups in the iris phenotype. In both treated and untreated mice at all three glaucomatous ages examined, IOP was significantly elevated compared with young preglaucomatous DBA/2J mice (P≤0.001). The degree of IOP elevation in treated mice was similar to that of untreated DBA/2J mice (P>0.3 for two-factor ANOVA for treatment and age). This result indicates that RGCs of both the treated and untreated groups were exposed to similar pressure insults.

Treated and untreated mice were aged to 12 months, an age when the majority of DBA/2J eyes have severe glaucomatous damage. Again, the treatment had an overwhelming protective effect and prevented detectable glaucomatous degeneration in the vast majority of nerves. The majority, 83%, of optic nerves from untreated 12-month-old DBA/2J mice had glaucomatous damage, and 73% were characterized by severe glaucoma. Severe glaucoma is defined as very substantial reductions in the number of healthy axons and the presence of many sick and dying axons. In contrast, only 5% of treated 12-month-old mice had any detectable glaucomatous damage, and only 3% had severe glaucoma. Numbers of nerves with each optic nerve grade were: 12-month untreated (62 total), 10 mild, 6 moderate, and 46 severe; 12-month treated (61 total), 58 mild, 1 moderate, and 2 severe. The mild stage occurs in normal mice with age and is not considered glaucoma.

To further assess the duration of the protective effect, a subset of mice was aged to 14 months. In agreement with findings at 12 months of age, treatment had conferred almost complete protection from glaucoma. At 14 months of age, only about 3% of treated mice had detectable glaucomatous damage.

To determine if there was subtle axon loss in treated nerves that had no obvious glaucomatous damage, axons were counted in the nerves of 10 randomly selected treated mice and compared with the nerves of young preglaucomatous DBA/2J mice.

Demonstrating the profound protective effect of the presently described treatment, no significant difference in axon number was detected (young preglaucomatous DBA/2J mice 51,554±1,332, n=8; graded mild treated DBA/2J mice, 48,625±2,309, n=10, P=0.3).

Finally, multiple other assays on a subset of eyes also demonstrated a striking prevention of glaucomatous damage. Treated mice had no obvious change in the number or morphology of somas in the RGC layer, whereas untreated mice had massive soma loss. Retinal and optic nerve morphology also appeared normal in the treated mice, whereas nontreated DBA/2J mice had clear loss of RGC axons and optic nerve head atrophy.

Example 2—Method for Focused Radiation Treatment to the Head and Eye Region

The present example is provided to demonstrate the utility of the invention for providing a treatment for glaucoma using radiation targeted at a specific area of the body, such as the head, and not the whole body. In addition, the present example demonstrates that this method is as effective at treating glaucoma as a either a combination therapy of whole body radiation plus bone marrow transfer or individually.

The apparatus depicted at FIG. 5 was employed to deliver radiation to the head area of a mouse model for glaucoma, specifically a DBA/2J mouse. The data obtained from these studies is presented in the bar graph of FIG. 4. As is demonstrated, the head-only radiation treatment without bone marrow treatment of these animals resulted in a significant reduction in the severity of observable glaucomatous optic nerve damage (95% of animals demonstrating only mild age-related optic nerve damage, 5% demonstrating only moderate glaucomatous optic nerve damage, 0% demonstrating severe glaucomatous optic nerve damage), compared to those animals that received whole-body radiation treatments alone (40% of animals demonstrating only mild age-related glaucomatous optic nerve damage, 0% demonstrating only moderate glaucomatous optic nerve damage, 60% demonstrating severe glaucomatous optic nerve damage).

In animals treated with whole body radiation and bone marrow, the protective effect against glaucomatous optic nerve damage was also significant and robust (90% of animals demonstrating only mild age-related optic nerve damage, 8% demonstrating only moderate glaucomatous optic nerve damage, 2% demonstrating severe glaucomatous optic nerve damage). These results are compared to the control group of animals that did not receive radiation treatment or radiation, in which 70% of the animals demonstrated severe glaucomatous optic nerve damage, 8% evidenced moderate glaucomatous optic nerve damage, and 20% of the animals demonstrated mild age-related optic nerve damage.

The bar graph in FIG. 4 presents the data obtained using a full-body irradiation treatment regimen and the data obtained with a head-only focused radiation treatment of a DBA/2J glaucoma model mouse.

Example 3—Method of Treatment for Human Glaucoma

The present example is presented to describe the anticipated protocol to be used in the practice of the present invention for the treatment of glaucoma in humans. In particular, the present invention is provided to demonstrate an anticipated treatment for inhibiting and/or reducing human glaucoma, particularly those hereditary forms of glaucoma. By way of example, such hereditary forms of human glaucoma in humans have been described in relation to genetic changes that occur over time.

In order to reduce the amount of radiation exposure to healthy tissue, as well as to reduce the amount of dose inhomogeneity, a procedure known as intensity modulated radiotherapy (IMRT) will be used to administer the appropriate radiation dose the a focused region of the head, and particularly the ocular region. IMRT is described in Nutting et al. (2000)[39], which reference is specifically incorporated herein by reference for this purpose.

Techniques for providing a directed dose of radiation to a desired isolated region of the human body have been developed for the treatment of cancer of the eye (e.g., retinoblastoma, uveal melanomas). In particular, L. Labroso-Le Rouic et al. (2004)[41] describes the technique of brachytherapy, which reference is specifically incorporated herein by reference. Accordingly, the method of the present invention may provide for a focused dose of radiation exposure to the eye using a brachytherapy technique of delivery (radioactive material sealed in needles, seeds, wires, or catheters, and placed directly in the eye region) in the doses as described herein. It is expected that the doses may be significantly reduced in actual practice with the same or similar therapeutic effects according to the present invention. For example, radiation dose ranges of about 1 Gy to about 15 Gy, or in a range of about 5 Gy to about 10 Gy, may be used.

These radiation administration techniques may be used in accomplishing the practice of the present methods to provide a treatment for glaucomal and ocular degeneration.

Example 4—Screening Method for Neuroprotective Agents and Therapeutic Regimens

The present example is provided to demonstrate the utility of the present invention for use as a screening tool to identify agents and/or treatments useful in the treatment, inhibition and/or progression of neurodegeneration, particularly neurodegeneration that occurs as a consequence of age.

In yet another aspect, the invention provides for a method of selecting and screening candidate substance and or treatments for degenerative diseases, particularly degenerative diseases of the eye, such as those that accompany the onset and progression of glaucoma. The method comprises the use of a model for selecting glaucoma-associated neurodegenerative inhibiting agents in an animal, this model being a DBA/2J mouse. In particular, the method comprises administering to an area of interest of a test animal having glaucoma-associated neurodegeneration an amount of a test agent, and measuring the amount of glaucoma-associated neurodegeneration in the animal to provide a potential neuroprotective activity test value; administering to an area of interest of a control animal having glaucoma-associated neurodegeneration an effective amount of radiation and measuring the amount of glaucoma-associated neurodegeneration in said animal to provide a control neuroprotective baseline value for a glaucoma-associated neuroprotective agent; comparing the test value to the control neuroprotective baseline value; and selecting a test agent that demonstrates a test value of 50% or more of the control neuroprotective baseline value in inhibiting of glaucoma-associated neurodegeneration.

In selecting an effective neuroprotective agent and/or treatment, agents and/or radiation levels of intensity may alternatively be selected on the basis of observed differences in degeneration levels observed between a glaucoma—afflicted animal that has received the test treatment and/or radiation level being examined and that degeneration level observed in a glaucoma—afflicted animal that has not received the neuroprotective agent and/or treatment. In this manner, potential neuroprotective agents and/or treatments or radiation levels will be selected that result in an observable degeneration level that is less than that observed in an untreated glaucoma-afflicted animal.

Figure 7:
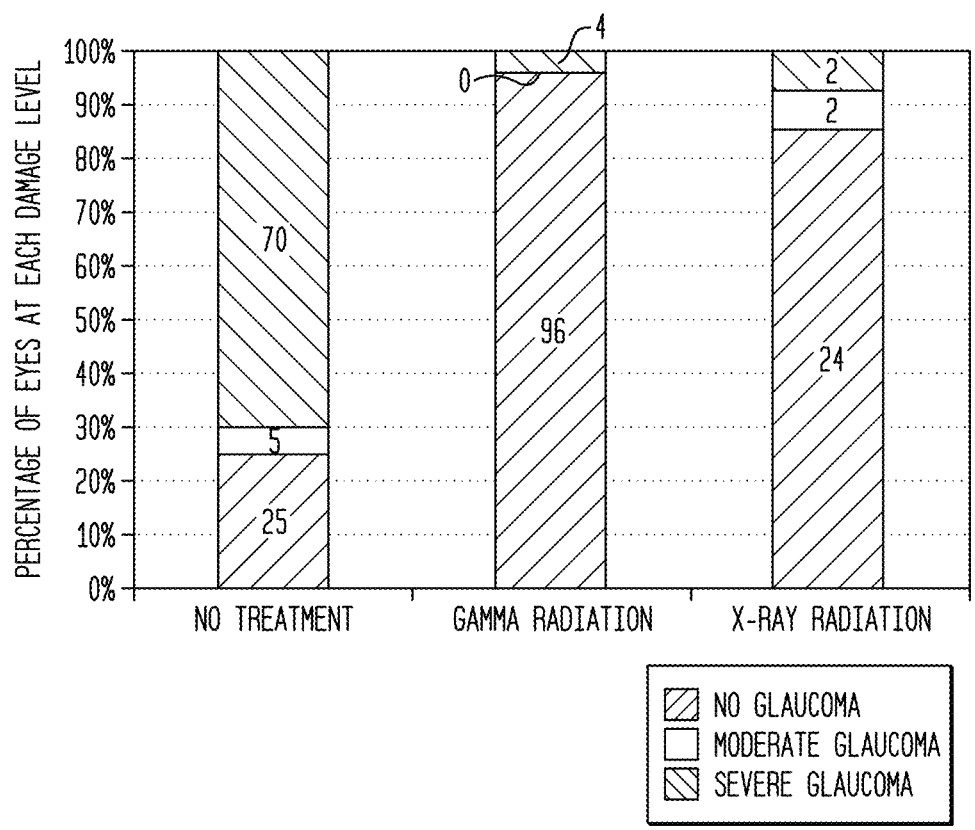
FIG. 7 is a bar graph comparing the effects on glaucoma of: no treatment, treatment with gamma radiation, and treatment with x-ray radiation in accordance with an embodiment of the invention.

Example 5—Comparison of Gamma Radiation and X-Ray Radiation on Protectively Inhibiting Glaucoma In this experiment, the effect of administering gamma radiation and x-ray radiation to each eye of DBA/2J mice (2-3 months of age), relative to no treatment with any radiation as the control, is evaluated. Gamma radiation is administered whole body to the DBA/2J mice according the procedure of Experiment 1 using the apparatus shown in FIG. 5. X-ray radiation (720 rads) is administered to each eye of the DBA/2J mice over a 4 minute period using apparatus 600 shown in FIG. 6. The treated and untreated mice are harvested at 12 months of age and the eyes thereof evaluated for glaucoma according to the procedure described in paragraphs above. The results of that evaluation are shown in the bar graph of FIG. 7. The results for the x-ray radiation treatment represent 14 treated DBA/2J mice. As shown in FIG. 7, treatment with x-ray radiation provided protective inhibition of glaucoma in the DBA/2J mice when compared to the untreated DBA/2J mice and the DBA/2J mice treated with gamma radiation.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart there from.

BIBLIOGRAPHY

The following references are specifically incorporated herein by reference in their entirety.
1. Ritch, R., et al. (1996), *The Glaucomas* (Mosby, St. Louis);
2. Weinreb, R. N. & Khaw, P. T. (2004), *Lancet* 363: 1711-1720;
3. Heijl, A., et al. (2002), *Arch. Ophthalmol.*, 120: 1268-1279;
4. Collaborative Normal-Tension Glaucoma Study Group (1998), *Am. J. Ophthalmol.*, 126: 487-497;
5. John, S. W., et al. (1999), *J. Glaucoma*, 8: 400-412;

6. John. S. W., et al. (1998), *Invest. Ophthalmol. Visual Sci.,* 39: 951-962;
7. Chang, B., et al. (1999), *Nat. Genet.,* 21: 405-409;
8. Anderson. M. G., et al (2002), *Nat. Genet.,* 30: 81-85;
9. Quigley, H. A., (1998), *Prog. Retin. Eye Res.,* 18: 39-57;
10. Nickells, R. W. (2004), *Brain Res. Bull.* 62: 439-446;
11. Raff, M. C., et al. (2002), *Science,* 296: 868-871;
12. Robert A. Good (July, 2000), *World Journal of Surgery,* 24(7): 797-810;
13. Clift, R. A., et al. (1991), *Blood,* 77(8): 1660-1665;
14. Matthews, D. C., et al. (1995), *Blood,* 85(4): 1122-1131;
15. Mackall, C. L., et al. (1997), *Blood,* 89(10): 3700-3707;
16. Roux, E., et al., (1996), *Blood,* 87(9): 3984-3992;
17. Champlin, R., et al. (1990), *Hematol. Oncol. Clin. North Am.,* 4: 687;
18. O'Reilly, R. J., et al. (1992), *Semin. Hematol.,* 29(1): 20;
19. Martin, P. J. et al. (1985), *Blood,* 66: 664;
20. Prentice, H. G., et al. (1982), *Lancet,* 1: 700;
21. Waldmann, H., et al. (1984), *Lancet,* 2: 483;
22. Antin, J. H., et al. (1991), *Blood,* 78: 2139;
23. De Witte, T., et al. (1986), *Blood,* 67: 1302;
24. Maraninchi, D. et al. (1988), *Transplant Int.,* 1: 91;
25. Soiffer, R. J. et al. (1992), *J. Clin. Oncol.,* 10: 1191;
26. Filipovich, A. H., et al. (1990), *Transplantation,* 50: 410;
27. Wagner, J. E. et al. (1990), *Blood,* 75: 1370;
28. Herve, P., et al. (1985), *Transplantation,* 39: 138;
29. Belkacemi, Y. et al. (1998), *Strahlenther Onkol.,* 174(2): 92-104;
30. Burt, Richard K., et al. (1998), *Blood,* 92(10): 3505-3514;
31. Horning, S. J., et al. (1994), *J. Clin. Oncol.,* 12: 2552;
32. Thomas, E. D. and Storb, R. (1970), *Blood,* 36(4): 507-515;
33. Buckner, C. D. et al. (1984), *Blood,* 64: 630-634;
34. Bortin, M. M. and Buckner, C. D. (1983), *Exp. Hematol.,* 11: 916-921;
35. Kessinger, A., and Armitage, J. O., (1987), *Bone Marrow Transplant,* 2: 15-18;
36. John, et al. (1988), *Invest. Opthalmol. Visual Sci.,* 39: 951-962.
37. Chang et al. (1999), *Nat. Genet.,* 21: 405-409.
38. Anderson, et al. (2002), *Nat. Genet.,* 30: 81-85.
39. Nutting et al. (2000), *The British Journal of Radiology,* 73: 459-469.
40. Sanderson, R. J. and Ironside, J. A. D. (2002), *BMJ,* 325(7368): 822-827.
41. Lumbroso-Le Rouic, et al., (2004) *Eye,* 18: 911-916.
42. Kipnis, J., et al. (2004), *European Journal of Neuroscience,* 19: 1191-1198.
43. Bakalash, S., et al. (2005), *J. Mol. Med.,* 83(11): 904-916.
44. Bakalash, S., Schwartz, et al. (2005), Department of Neurobiology, *The Weizmann Institute of Science.*
45. Takeda, A., et al. (1999), *Int. J. Radiation Oncology Biol. Phys.,* 44(3): 599-605.
46. Phillips, C., et al. (2003), *Australasian Radiology,* 47: 226-230.
47. Million, Rodney R., and Parsons, James T. (1999), *Front. of Radiat. Ther. Oncol.,* 32: 21-33.
48. Anderson, M. G., et al. (2005), *PNAS,* 102(12): 4566-4571.
49. Sanderson, R. J. and Ironside, J. A. D. (2002), *BMJ,* 325(7368): 822-827.
50. Nag, Subir, et al. (2003), *International Journal of Radiation Oncology, Biology and Physics,* 56(2): 544.
51. Cancer, Principles & Practice of Oncology, Publisher: Philadelphia: Lippincott-Raven, Publication Date: c1997. DeVita, Vincent T., Hellman, Samuel, Rosenberg, Steven A.
52. Anderson et al. (2005), *PNAS,* 102(12): 4566-4571.

---

What is claimed is:

1. A method of treating neurodegeneration, the method comprising the steps of: administering a treatment regimen comprising administering radiation in a neurodegeneration-inhibiting amount to a head or eye area of a subject having glaucoma, to thereby further inhibit the eye of the subject against neurodegeneration caused by glaucoma, wherein radiation is delivered to the subject prior to an incision to the eye.

2. The method of claim 1, wherein the radiation interacts with tissue in the retina.

3. The method of claim 1, wherein the radiation interacts with tissue in the optical disk.

4. The method of claim 1, wherein the radiation interacts with tissue in the optic nerve.

5. The method of claim 1, wherein the radiation is gamma radiation.

6. The method of claim 5, wherein the gamma radiation is applied to the eye and penetrates the eye to at least the retina to interact with tissue in the retina.

7. The method of claim 5, wherein the gamma radiation is applied to the eye and penetrates the eye to at least the retina to interact with tissue in the optic disk.

8. The method of claim 5, wherein the gamma radiation is applied to the eye and penetrates the eye to at least the retina to interact with tissue in the optic nerve.

9. The method of claim 5, wherein the gamma radiation dose is in the range of about 8 Grays (Gy) to about 15 Grays (Gy).

10. The method of claim 5, wherein the gamma radiation dose is in the range of about 1.0 Gy to about 5.0 Gy.

11. The method of claim 5, wherein the gamma radiation dose is about 2.5 Gy.

12. The method of claim 1, wherein the radiation is x-ray radiation.

13. The method of claim 12, wherein the x-ray radiation is applied to the eye and penetrates the eye to at least the retina to interact with tissue in the retina.

14. The method of claim 12, wherein the x-ray radiation is applied to the eye and penetrates the eye to at least the retina to interact with tissue in the optic disk.

15. The method of claim 12, wherein the x-ray radiation is applied to the eye and penetrates the eye to at least the retina to interact with tissue in the optic nerve.

16. The method of claim 12, wherein the x-ray radiation dose is in the range of about 8 Gy to about 15 Gy.

17. The method of claim 12, wherein the x-ray radiation dose is in the range of about 1.0 Gy to about 5.0 Gy.

18. The method of claim 12, wherein the x-ray radiation dose is about 2.5 Gy.

19. The method of claim 1, wherein the radiation dose is in the range of about 8 Gy to about 15 Gy.

20. The method of claim 1, wherein the radiation dose is in the range of about 1.0 Gy to about 5.0 Gy.

21. The method of claim 1, wherein the radiation dose is about 2.5 Gy.

22. The method of claim 1, wherein the form of glaucoma is an age-related hereditary form of glaucoma.

23. The method of claim 1, wherein the radiation is administered as two or more approximately equal radiation doses.

24. The method of claim 1, wherein the neurodegeneration-inhibiting amount of x-ray radiation administered provides a delivery area to the head or eye area of the subject having a diameter of at least about 10 microns.

25. The method of claim 1, wherein the neurodegeneration-inhibiting amount of x-ray radiation administered provides a delivery area having a diameter of at least about 50 microns.

26. The method of claim 1, wherein the subject has an intraocular pressure (IOP) less than or equal to 16 mm Hg.

27. The method of claim 1, wherein the subject has a genetic precursor for developing neurodegeneration.

28. The method of claim 27, wherein the precursor is selected from the group consisting of GLC1A (1q24), GLC1B (2-cen-q13), GLC1C (3q21-q24), GLC1D (8q23), GLC1E (10p14-p15), GLC1F (7q35-q36), GLC3A (2p21 Cytochrome), P4501B1 (CYP1B1), GLC3B (1p36.2-36.1), Tyrp1 and Gpnmb.

29. The method of claim 1, wherein a cup to disc ratio of the subject is less than 0.5.

* * * * *